(12) United States Patent
Eliav et al.

(10) Patent No.: US 8,020,238 B2
(45) Date of Patent: Sep. 20, 2011

(54) POWERED TOOTHBRUSH

(75) Inventors: Eyal Eliav, New York, NY (US);
Kyoungeun Ahn, New York, NY (US);
John J. Gatzemeyer, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 12/194,056

(22) Filed: Aug. 19, 2008

(65) Prior Publication Data

US 2009/0049626 A1    Feb. 26, 2009

Related U.S. Application Data

(60) Division of application No. 10/970,722, filed on Oct. 22, 2004, now Pat. No. 7,428,766, which is a continuation of application No. 10/066,459, filed on Jan. 31, 2002, now abandoned.

(51) Int. Cl.
*A61C 17/34* (2006.01)
(52) U.S. Cl. ............... 15/22.1; 15/22.2; 15/28
(58) Field of Classification Search .......... 15/22.1, 15/22.2, 28
See application file for complete search history.

(56) References Cited

U.S. PATENT DOCUMENTS

| 1,255,028 | A | 1/1918 | Leonard et al. |
| 1,796,641 | A | 3/1928 | Zimmerman |
| 2,140,307 | A | 12/1938 | Belaschk et al. |
| 2,215,031 | A | 9/1940 | Elmore |
| 2,379,049 | A | 8/1945 | Tompkins |
| 3,103,027 | A | 9/1963 | Birch |
| 3,230,562 | A | 1/1966 | Birch |
| 3,242,516 | A | 3/1966 | Cantor |
| 3,577,579 | A | 5/1971 | Duve et al. |
| 4,081,876 | A | 4/1978 | Pugh |
| 4,156,620 | A | 5/1979 | Clemens |
| 4,274,173 | A | 6/1981 | Cohen |
| 4,479,516 | A | 10/1984 | Hunter |
| 4,766,630 | A | 8/1988 | Hegemann |
| 4,795,347 | A | 1/1989 | Maurer |
| 4,827,550 | A | 5/1989 | Graham et al. |
| 4,845,795 | A | 7/1989 | Crawford et al. |

(Continued)

FOREIGN PATENT DOCUMENTS

CA     1082408     *  7/1980

(Continued)

OTHER PUBLICATIONS

European Search 09158251 mailed Aug. 3, 2009.

*Primary Examiner* — Randall Chin
(74) *Attorney, Agent, or Firm* — Judy W. Chung

(57) ABSTRACT

A powered toothbrush refill head combines a typical round oscillating or primary tuft block which oscillates in a rotational manner with a secondary tuft block. The secondary tuft block may be oscillated in a rotational manner or may oscillate linearly back and forth in the same direction as the handle of the toothbrush. The secondary tuft block could be in the form of a pair of side by side plates mounted on the head adjacent to the round oscillating block. The invention could also be practice where the secondary tuft block is in the form of a plurality of sets of rows of bristles mounted for back and forth movement in a direction perpendicular to the handle.

14 Claims, 23 Drawing Sheets

U.S. PATENT DOCUMENTS

| | | | |
|---|---|---|---|
| 4,894,880 A | 1/1990 | Aznavoorian | |
| 4,989,287 A | 2/1991 | Scherer | |
| 5,046,213 A | 9/1991 | Curtis et al. | |
| 5,068,939 A | 12/1991 | Holland | |
| 5,070,567 A | 12/1991 | Holland | |
| 5,077,855 A | 1/1992 | Ambasz | |
| 5,088,145 A | 2/1992 | Whitefield | |
| 5,099,536 A | 3/1992 | Hirabayashi | |
| D330,286 S | 10/1992 | Curtis et al. | |
| 5,170,525 A | 12/1992 | Cafaro | |
| 5,177,826 A | 1/1993 | Vrignaud et al. | |
| D334,473 S | 4/1993 | Volpenhein et al. | |
| 5,226,206 A | 7/1993 | Davidovitz et al. | |
| 5,259,083 A | 11/1993 | Stansbury, Jr. | |
| 5,335,389 A | 8/1994 | Curtis et al. | |
| 5,353,460 A | 10/1994 | Bauman | |
| 5,359,747 A | 11/1994 | Amakasu | |
| 5,392,483 A | 2/1995 | Heinzelman et al. | |
| 5,404,608 A | 4/1995 | Hommann | |
| 5,416,942 A | 5/1995 | Baldacci et al. | |
| 5,435,034 A | 7/1995 | Bigler et al. | |
| 5,446,940 A | 9/1995 | Curtis et al. | |
| 5,500,970 A | 3/1996 | Maurer et al. | |
| 5,504,958 A | 4/1996 | Herzog | |
| 5,504,959 A | 4/1996 | Yukawa et al. | |
| 5,504,960 A | 4/1996 | Hommann | |
| 5,524,312 A | 6/1996 | Tan et al. | |
| 5,617,601 A | 4/1997 | McDougall | |
| 5,617,603 A | 4/1997 | Mei | |
| 5,625,916 A | 5/1997 | McDougall | |
| 5,727,273 A | 3/1998 | Pai | |
| 5,732,432 A | 3/1998 | Hui | |
| 5,732,433 A | 3/1998 | Gocking | |
| 5,735,011 A | 4/1998 | Asher | |
| 5,764,743 A | 6/1998 | Goedken et al. | |
| 5,784,743 A | 7/1998 | Shek | |
| 5,799,354 A | 9/1998 | Amir | |
| 5,822,821 A | 10/1998 | Sham | |
| RE35,941 E * | 11/1998 | Stansbury, Jr. | |
| 5,836,030 A | 11/1998 | Hazeu | |
| 5,850,655 A | 12/1998 | Gocking et al. | |
| 5,876,206 A | 3/1999 | Maurer | |
| 5,974,613 A | 11/1999 | Herzog | |
| 6,000,083 A | 12/1999 | Blaustein et al. | |
| 6,006,394 A | 12/1999 | Bredall et al. | |
| 6,032,313 A | 3/2000 | Tsang | |
| 6,138,310 A | 10/2000 | Porper et al. | |
| D434,563 S | 12/2000 | Lim et al. | |
| 6,178,579 B1 | 1/2001 | Blaustein et al. | |
| 6,189,693 B1 | 2/2001 | Blaustein et al. | |
| 6,237,178 B1 | 5/2001 | Krammer | |
| 6,308,358 B2 | 10/2001 | Gruber et al. | |
| 6,314,606 B1 | 11/2001 | Hohlbein | |
| 6,360,395 B2 | 3/2002 | Blaustein et al. | |
| 6,371,294 B1 | 4/2002 | Blaustein et al. | |
| 6,434,773 B1 | 8/2002 | Kuo | |
| 6,453,498 B1 | 9/2002 | Wu | |
| 6,463,615 B1 | 10/2002 | Gruber et al. | |
| 6,510,575 B2 | 1/2003 | Calabrese | |
| 6,553,604 B1 | 4/2003 | Braun et al. | |
| 6,564,416 B1 | 5/2003 | Claire et al. | |
| 6,574,820 B1 | 6/2003 | DePuydt et al. | |
| 6,725,490 B2 | 4/2004 | Blaustein et al. | |
| 6,928,685 B1 | 8/2005 | Blaustein et al. | 15/22.1 |
| 6,952,854 B2 | 10/2005 | Blaustein et al. | 15/22.1 |
| 2001/0001334 A1 | 5/2001 | Gruber et al. | |
| 2001/0004781 A1 | 6/2001 | Blaustein et al. | |
| 2002/0032941 A1 | 3/2002 | Blaustein et al. | |
| 2002/0162180 A1 | 11/2002 | Blaustein et al. | |
| 2003/0066145 A1 | 4/2003 | Prineppi | |
| 2003/0084525 A1 | 5/2003 | Blaustein et al. | |
| 2003/0084526 A1 | 5/2003 | Brown et al. | |
| 2003/0084528 A1 | 5/2003 | Chan et al. | |
| 2003/0140435 A1 | 7/2003 | Eliav et al. | |
| 2003/0140436 A1 | 7/2003 | Gatzemeyer et al. | |
| 2003/0140437 A1 | 7/2003 | Eliav et al. | |
| 2003/0182743 A1 | 10/2003 | Gatzemeyer et al. | |
| 2003/0182744 A1 | 10/2003 | Fattori et al. | |
| 2003/0182746 A1 | 10/2003 | Fattori et al. | |
| 2003/0221270 A1 | 12/2003 | Kuo | |
| 2004/0010869 A1 * | 1/2004 | Fattori et al. | |
| 2004/0045105 A1 * | 3/2004 | Eliav et al. | |
| 2004/0049867 A1 * | 3/2004 | Hui | |
| 2004/0060133 A1 | 4/2004 | Eliav | |
| 2004/0060134 A1 * | 4/2004 | Eliav et al. | |
| 2004/0060135 A1 * | 4/2004 | Gatzemeyer et al. | |
| 2004/0060137 A1 * | 4/2004 | Eliav | |
| 2004/0083566 A1 * | 5/2004 | Blaustein et al. | |
| 2004/0084063 A1 * | 5/2004 | Vago et al. | |
| 2004/0123409 A1 * | 7/2004 | Dickie | |
| 2004/0143917 A1 * | 7/2004 | Ek | |
| 2004/0168272 A1 * | 9/2004 | Prineppi | |
| 2004/0177458 A1 * | 9/2004 | Chan et al. | |
| 2004/0177462 A1 | 9/2004 | Brown, Jr. et al. | |

FOREIGN PATENT DOCUMENTS

| | | | |
|---|---|---|---|
| CA | 2236827 Y | * | 10/1996 |
| CA | 2141569 | * | 1/2000 |
| CN | 2271352 Y | * | 12/1997 |
| CN | 2271353 Y | * | 12/1997 |
| CN | 2324988 Y | * | 6/1999 |
| DE | 27 36 286 | | 12/1978 |
| DE | 84 26 426.8 | | 3/1985 |
| DE | 3406112 A1 | | 8/1985 |
| DE | 44 12 301 A1 | | 10/1995 |
| DE | 296 00 236 U1 | | 4/1996 |
| DE | 296 13 608 U1 | | 11/1996 |
| DE | 296 18 755 U1 | | 3/1997 |
| DE | 298 09 977 U1 | | 2/1999 |
| DE | 298 21 121 U | | 3/1999 |
| DE | 103 15 011 A1 | | 5/2004 |
| EP | 0 208 401 B1 | * | 5/1991 |
| EP | 0 254 397 B1 | * | 7/1991 |
| EP | 0 460 610 A | | 12/1991 |
| EP | 0 488 971 A2 | * | 6/1992 |
| EP | 0 546 203 B1 | * | 8/1996 |
| EP | 0 520 985 B1 | * | 8/1997 |
| EP | 1 053 721 A1 | * | 11/2000 |
| EP | 1 059 049 A | | 12/2000 |
| EP | 1 093 770 A2 | * | 4/2001 |
| EP | 1 139 908 A1 | * | 5/2001 |
| EP | 1 132 057 A1 | * | 9/2001 |
| EP | 1 385 448 | | 11/2002 |
| EP | 1 386 589 A1 | | 2/2004 |
| EP | 1 093 770 B1 | * | 3/2004 |
| EP | 1 402 846 A2 | | 3/2004 |
| FR | 1250455 | | 12/1960 |
| FR | 2548528 | | 1/1985 |
| GB | 452961 | | 9/1936 |
| GB | 1583558 | | 1/1981 |
| GB | 2228861 A | | 9/1990 |
| GB | 2237505 A | | 5/1991 |
| GB | 2 247 297 | * | 2/1992 |
| GB | 2290224 A | | 12/1995 |
| GB | 2319170 A | | 5/1998 |
| JP | 3001895 | * | 6/1905 |
| JP | 57-89810 | * | 6/1982 |
| JP | 61-131706 | * | 6/1986 |
| JP | 62-49806 | * | 3/1987 |
| JP | 63-183822 | * | 11/1988 |
| JP | 1-066704 | | 3/1989 |
| JP | 1-141631 | | 9/1989 |
| JP | 2-22121 | | 2/1990 |
| JP | 2-218309 | | 8/1990 |
| JP | 4-77326 | | 7/1992 |
| JP | 4-133733 | | 12/1992 |
| JP | 5-146314 | | 6/1993 |
| JP | 5-161509 | | 6/1993 |
| JP | 5-199918 | | 8/1993 |
| JP | 5-269024 | * | 10/1993 |
| JP | 5-93253 | | 12/1993 |
| JP | 6-47298 | * | 2/1994 |
| JP | 6-189822 | * | 7/1994 |
| JP | 6505617 | * | 7/1994 |
| JP | 7-116023 | * | 5/1995 |
| JP | 7-116024 | * | 5/1995 |
| JP | 2511226 | * | 7/1996 |

| | | | | | | | |
|---|---|---|---|---|---|---|---|
| JP | 9-168496 | * | 6/1997 | WO | WO 97/24079 | | 7/1997 |
| JP | 2811246 | * | 8/1998 | WO | WO 98/23223 | | 6/1998 |
| JP | 11-501247 | * | 2/1999 | WO | WO 99/23910 | | 5/1999 |
| JP | 3063406 | * | 8/1999 | WO | WO 00/39379 | | 7/2000 |
| JP | 11-342140 | * | 12/1999 | WO | 00/76369 | A | 12/2000 |
| JP | 2000-505690 | * | 5/2000 | WO | WO 00/74592 | A1 | 12/2000 |
| JP | 2000-507489 | * | 6/2000 | WO | WO 00/78244 | A1 | 12/2000 |
| KR | 91-700015 | * | 3/1991 | WO | WO 01/21094 | A1 | 3/2001 |
| TW | 239963 | * | 2/1905 | WO | WO 01/32095 | A1 | 5/2001 |
| TW | 135303 | * | 5/1905 | WO | WO 01/89344 | A2 | 11/2001 |
| TW | 257968 | * | 6/1905 | WO | WO 01/91603 | | 12/2001 |
| TW | 154730 | * | 3/1979 | WO | WO 02/87454 | A1 | 11/2002 |
| TW | 164493 | * | 7/1979 | WO | WO 03/020159 | A1 | 3/2003 |
| TW | 200863 | * | 5/1981 | WO | 03/039393 | A | 5/2003 |
| TW | 274724 | * | 4/1984 | WO | WO 03/039393 | A1 | 5/2003 |
| TW | 311444 | | 12/1985 | WO | WO 03/039394 | A1 | 5/2003 |
| TW | 135303 | | 6/1990 | WO | WO 03/039395 | A2 | 5/2003 |
| TW | 137856 | * | 7/1990 | WO | WO 03/039396 | A1 | 5/2003 |
| TW | 212909 | * | 9/1993 | WO | WO 03/039397 | A1 | 5/2003 |
| TW | 253174 | * | 8/1995 | WO | WO 03/063723 | A1 | 8/2003 |
| TW | 334345 | | 6/1998 | WO | WO 03/077790 | A1 | 9/2003 |
| TW | 406557 | | 9/2000 | WO | WO 2004/028294 | A1 | 4/2004 |
| WO | WO 90/09123 | | 8/1990 | WO | WO 2004082428 | | 9/2004 |
| WO | WO 95/11636 | | 5/1995 | | | | |
| WO | WO 96/37164 | | 11/1996 | | | | |

* cited by examiner

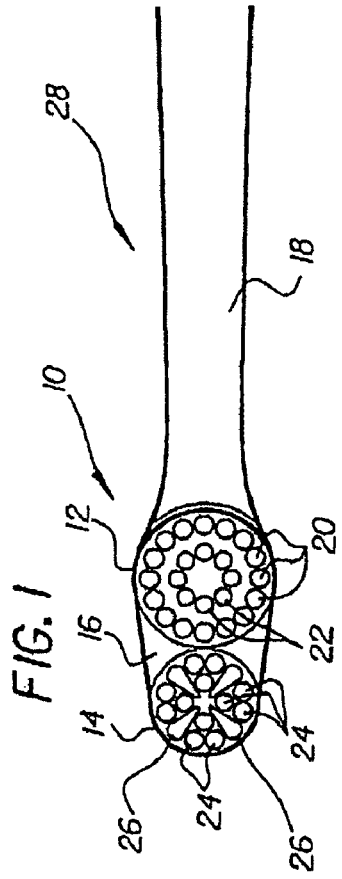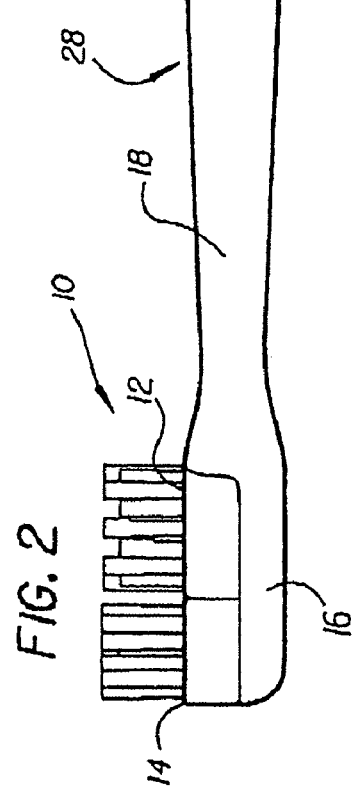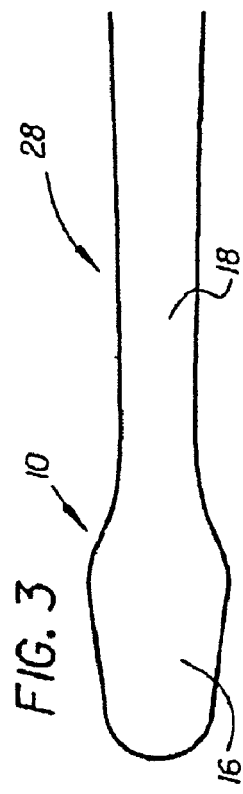

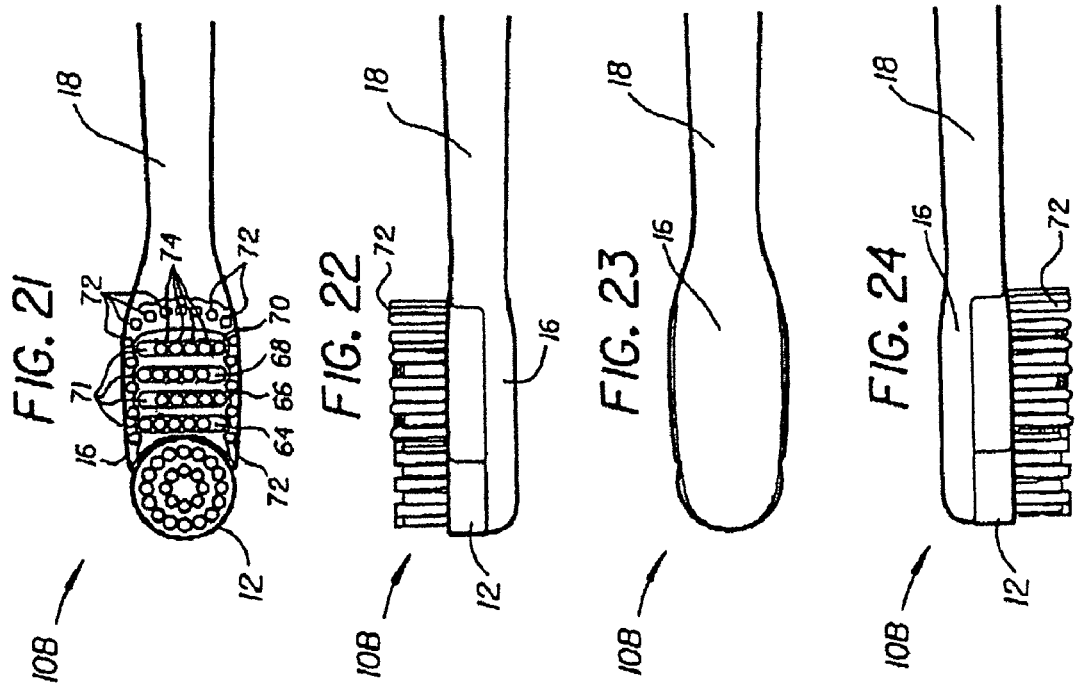

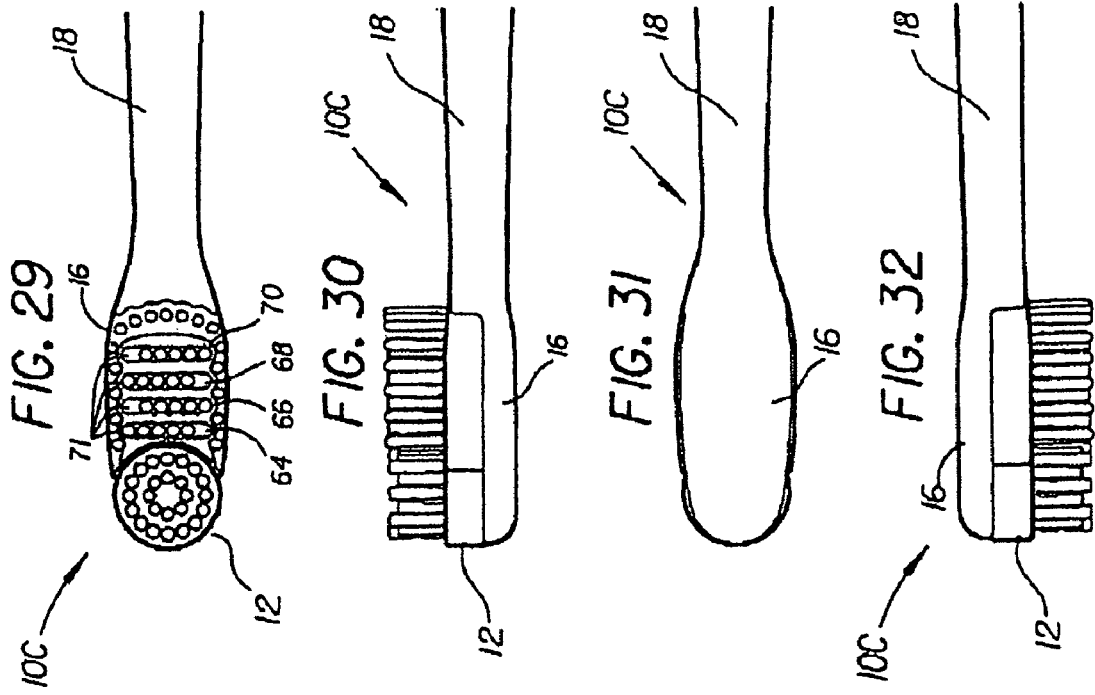

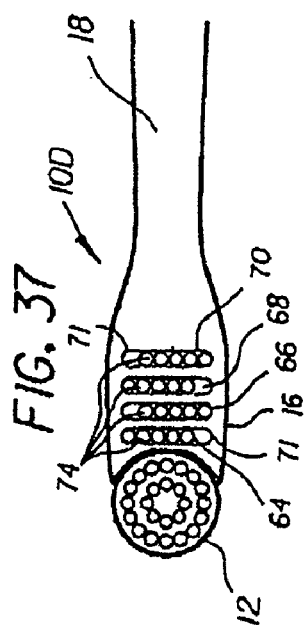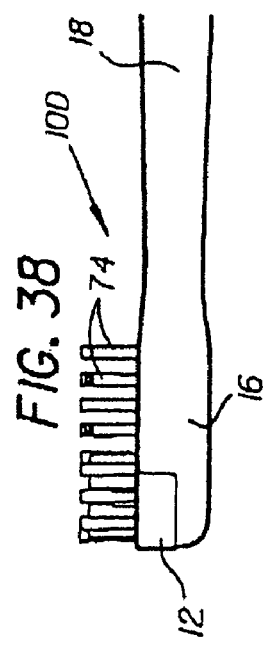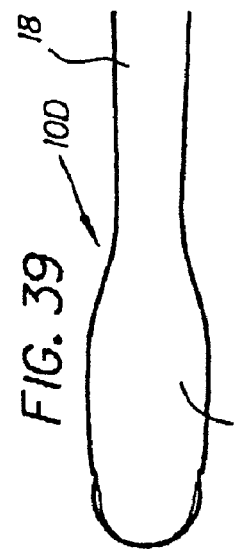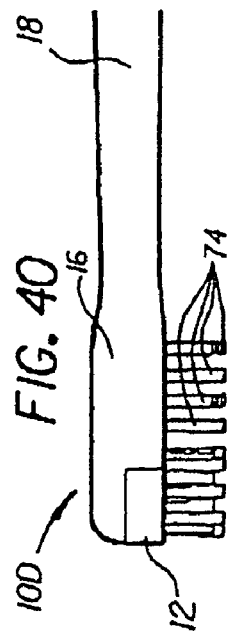

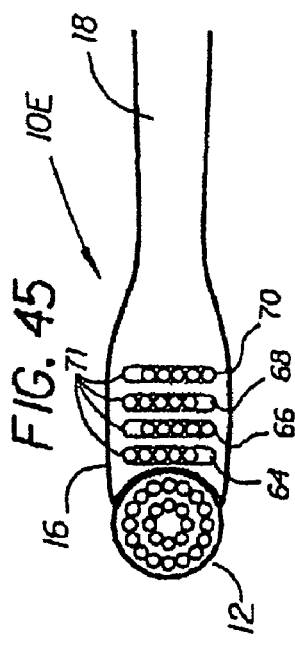
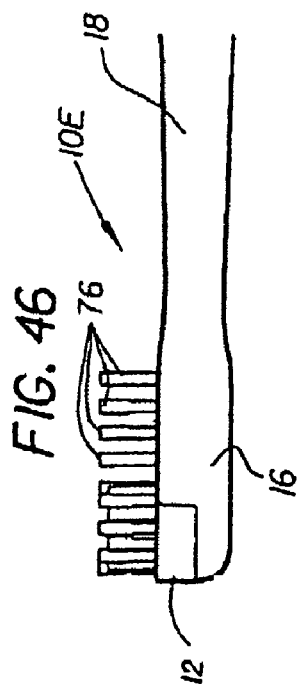
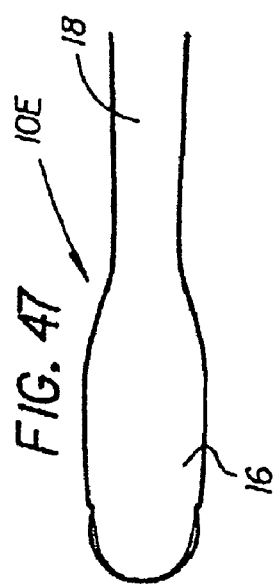
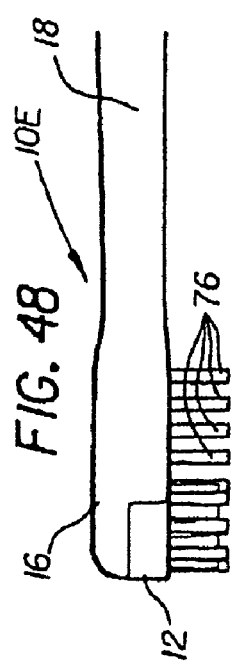

United States Patent US 8,020,238 B2

POWERED TOOTHBRUSH

CROSS-REFERENCE TO RELATED APPLICATIONS

The present application is a divisional of U.S. patent application Ser. No. 10/970,722, filed on Oct. 22, 2004 and now U.S. Pat. No. 7,428,766, which is a continuation of U.S. patent application Ser. No. 10/066,459, filed on Jan. 31, 2002 and now abandoned, the entireties of which are hereby incorporated by reference.

BACKGROUND OF THE INVENTION

The present invention is directed to a powered toothbrush refill head that includes an oscillating block having bristles. Various types of such toothbrushes are generally known in the art. Reference is made to U.S. Pat. No. 5,625,916 which relates to an electrically driven toothbrush which includes a motor drive for rotating a drive shaft. The drive shaft is connected to a bristle holder on the head of the toothbrush in such a manner that rotation of the drive shaft causes the bristle holder to rotationally oscillate back and forth. Various other arrangements are known for oscillating a bristle holder mounted to the head of an electric toothbrush.

U.S. Pat. No. 5,416,942 describes a motorized toothbrush having two concentrically arranged brushes coaxially supported in a shell. The brushes are driven by a drive shaft connected to a spindle which is bent to form two inclined arms at its end. Each of the arms is located in a slot in each respective brush. When the drive shaft is rotated the inclined aims cause each brush to rotate about their axis in opposite directions to each other.

The motorized toothbrush described in PCT International Publication No. WO 00/78244 similarly includes two coaxially mounted first and second brush heads which rotationally oscillate with respect to each other in different directions and/or at different speeds. Two different drive mechanisms are disclosed. One drive mechanism includes a linearly reciprocating actuator to which two connecting rods are attached. The connecting rods are formed from a single piece of wire generally V-shaped with an end of each connecting rod being mounted to a different one of the brush heads. As the actuator and connecting rods are moved linearly back and forth the ends of the connecting rods are moved toward and away from each other to cause the brush heads to rotate. In the second embodiment each brush head is provided with a toothed region which engages a conical year at the distal end of a rotationally oscillating shaft so that rotational oscillation of the shaft is transmitted by the conical gear to each toothed region to thereby rotationally oscillate the brush heads.

U.S. Pat. No. 5,836,030 discloses a rather complicated arrangement for a dental cleaning device having two brush holders. One of the brush holders is reciprocated about a pivotal axis as a result of a pivotal coupling between the brush holder and a connecting rod in the drive means. The other brush holder is also reciprocated about a pivotal axis as a result of a coupling between the brush holder and a drive member of the drive means. Although the two brush holders are located adjacent to each other the reciprocation of one of the brush holders is not utilized to cause the reciprocation of the other brush holder. Instead, both brush holders oscillate as a result of each brush holder being coupled to the drive means.

U.S. Pat. No. 6,237,178 discloses a toothbrush having a bristle holder which is rotated reciprocally along a circularly arcuate path. An interdental bristle holder is mounted longitudinally outwardly of the bristle holder. The patent states that the interdental bristle holder is reciprocatingly movable transversely to the longitudinal axis and is in driving engagement with the bristle holder so that the interdental bristle holder reciprocates transversely to the longitudinal axis when the bristle holder is reciprocated along the circularly arcuate path. The drawings, however, illustrate the interdental bristle holder to have an arcuate edge which is parallel to and extends partially around the arcuate edge of the bristle holder 40. Accordingly, there would be little room for any significant transverse reciprocation.

U.S. Pat. No. 6,308,358 discloses a toothbrush having a bristle holder and an interdental bristle holder. The patent states that each of these bristle holders performs a pivotal movement along a circular path, but does not state how the bristle holders are driven.

U.S. Pat. No. 3,242,516 discloses a toothbrush having a central set of bristles with a further set of bristles on each side thereof. The central set is driven by a drive mechanism. The central set includes a gear which meshes with gears for each of the other two sets so that rotation of the central set of brush elements will cause the other sets of brush elements to also rotate. No mention is made of rotating the brush elements back and forth in an oscillating manner.

U.S. Pat. No. 5,353,460 discloses a power driven toothbrush which uses a rather complicated drive arrangement including various types of gears and modified shaft structure to rotationally oscillate a brush carrier. The brush carrier is linked to a brush holder so that the brush holder is also rotationally oscillated.

U.S. Pat. No. 5,504,959 discloses an electric toothbrush wherein a pair of rotating bases holding brush bundles is rotatably mounted in a pair of pins secured to a slider. A pinion is secured to each base for engagement with a rack of a holder. The slider is mounted in the holder and moved longitudinally by a drive mechanism. As the slider moves longitudinally the engagement or the pinions with the rack causes the bases to rotate in a reciprocating motion to thereby reciprocatingly rotate the brush bundles.

PCT International Publication No. WO 01/91603 discloses a toothbrush having sets of bristle tufts which reciprocate in their angular orientation.

SUMMARY OF THE INVENTION

An object of this invention is to provide a powered toothbrush refill head which is capable of delivering a cleaning, polishing, whitening action in addition to the cleaning efficiency of a typical powered toothbrush refill product.

A further object of this invention is to provide various techniques for adding to the cleaning efficiency of an oscillating block in the toothbrush head.

In accordance with this invention the toothbrush head includes a primary tuft block mounted to the head. The primary tuft block is mounted in such a manner as to oscillate back and forth preferably rotationally. The head includes a secondary tuft block which is driven to further oscillate back and forth while the primary tuft block is oscillated back and forth.

In one practice of this invention the secondary tuft block is interconnected with the primary tuft block so that oscillating rotation of the primary tuft block causes an oscillating rotation of the secondary tuft block.

In accordance with a further practice of this invention the secondary tuft block comprises a plurality of side by side plates connected to the primary tuft block in such a manner that the side by side plates oscillate linearly in a direction parallel to the handle of the toothbrush while the primary tuft block is oscillating.

In still yet another practice of this invention the secondary tuft block is a plurality of rows of bars extending, laterally across the head perpendicular to the handle. The bars oscillate back and forth across the tuft head in a direction perpendicular to the handle while the primary tuft block is oscillating.

THE DRAWINGS

FIG. 1 is a top plan view of a powered toothbrush refill head in accordance with one practice of this invention;

FIG. 2 is a side elevational view of the head shown in FIG. 1;

FIG. 3 is a bottom plan view of the head shown in FIGS. 1-2;

FIG. 21 is a top plan view of a powered toothbrush refill head in accordance with yet another embodiment of this invention;

FIG. 22 is a side elevational view of the head shown in FIG. 21;

FIG. 23 is a bottom plan view of the head shown in FIG. 22;

FIG. 24 is a view similar to FIG. 22 showing the head inverted;

FIG. 29 is a top plan view of a variation of the powered toothbrush refill head shown in FIGS. 21-28;

FIG. 30 is a side elevational view of the head shown in FIG. 29;

FIG. 31 is a bottom plan view of the head shown in FIGS. 29-30;

FIG. 32 is a view similar to FIG. 30 with the head inverted;

FIG. 37 is a top plan view of yet another variation of the powered toothbrush refill head shown in FIGS. 21-28;

FIG. 38 is a side elevational view of the head shown in FIG. 37;

FIG. 39 is a bottom plan view of the head shown in FIGS. 37-38;

FIG. 40 is a view similar to FIG. 38 with the head inverted;

FIG. 45 is a top plan view of still yet another variation of the powered toothbrush refill head shown in FIGS. 21-28;

FIG. 46 is a side elevational view of the head shown in FIG. 45;

FIG. 47 is a bottom plan view of the head shown in FIGS. 45-46;

FIG. 48 is a view similar to FIG. 46 showing the head in an inverted position;

DETAILED DESCRIPTION

Figure 5:
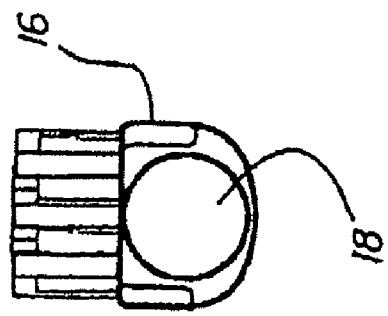
FIGS. 4-5 are end elevational views of the head shown in FIGS. 1-3.
Figure 4:
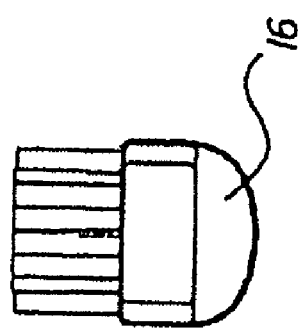
Figure 6:
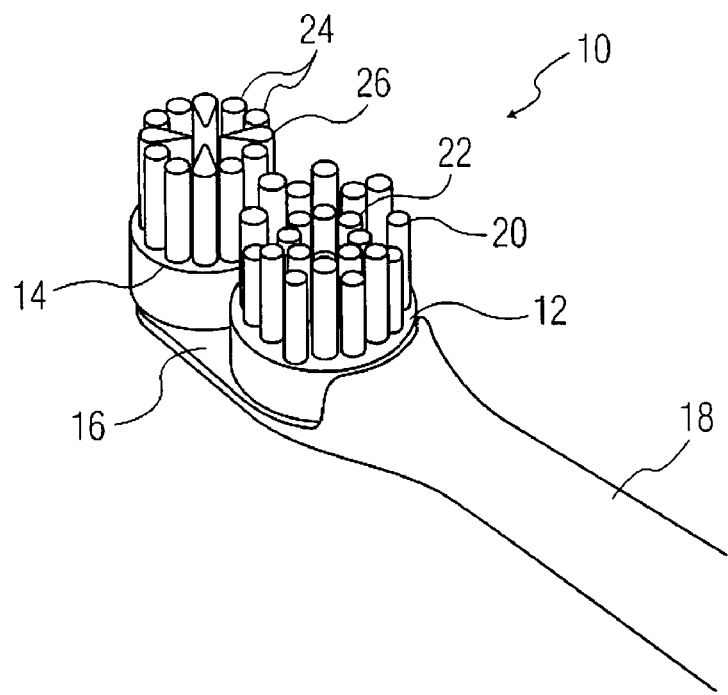
FIGS. 6-7 are perspective views of the head shown in FIGS. 1-5 in the upright and inverted positions.
Figure 7:
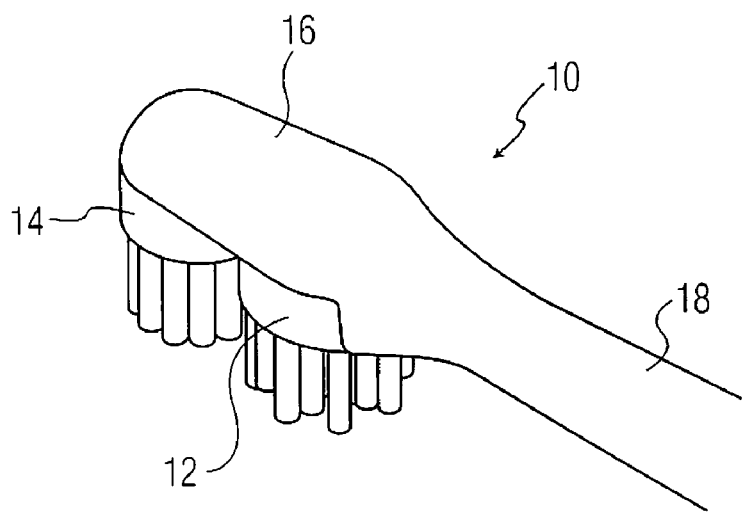

FIGS. 1-10 are directed to a practice of the invention wherein a powered toothbrush refill head 10 is provided with a primary tuft block 12 and a secondary tuft block 14 mounted to the refill arm 16 of a toothbrush 28 at the end of handle extension 18 at a location displaced from the primary tuft block. Each tuft block contains various types of bristles or brushing elements. As shown, for example, in FIGS. 1-2 and 6-7 the primary tuft block 12 has a plurality of bristles arranged in any suitable pattern. For example, an outer generally circularly arranged row of natural bristles 20 is located around the periphery of tuft block 12. An inner set of natural bristles 22 is located in a generally circular pattern concentrically within the circular arrangement of outer bristles 20. As illustrated in FIGS. 2 and 6 some of the bristles are shorter than other bristles.

As shown each of primary tuft block 12 and secondary tuft block 14 is of generally circular cross-sectional shape. Secondary tuft block 14 is located outwardly of primary tuft block 12 and is of smaller size than primary tuft block 12.

Secondary tuft block 14 also includes a plurality of bristles. In the illustrated embodiment these bristles include four sets of natural bristle tufts 24 separated from each other by rubber bristles or massage elements 26 which are of the same height as bristles 24.

It is to be understood that the specific illustration and description of the bristles for primary tuft block 12 and secondary tuft block 14 is merely for exemplary purposes. The invention can, however, be practiced with various combinations of the same or different bristle configurations (such as stapled, IMT, etc.) and/or with the same or different bristle materials (such as nylon bristles, spiral bristles, rubber bristles, etc.). It is thereby possible to select the combination of bristle configurations and bristle materials to achieve specific intended results, such as to create as much movement from the oscillating tuft heads to deliver additional oral health benefits like enhanced cleaning, tooth polishing and/or tooth whitening.

It is also to be understood that the head 16 could include other bristles such as on non-movable portions of the heads separate from the bristles on the oscillating tufts blocks 12, 14. Thus, for example, rubber triangular bristles or massage elements could be located on opposite portions of the head 16 between the tuft blocks 12 and 14. It is also to be understood that the bristles for the oscillating tuft blocks could include combinations of natural or rubber bristles or could include solely natural or solely rubber bristles.

It is to be understood that as used herein the term bristle is meant to include cleaning elements which may be of solid construction such as rubber massage members or stimulators and is not intended to be limited to tufts or natural bristles.

Figure 8:
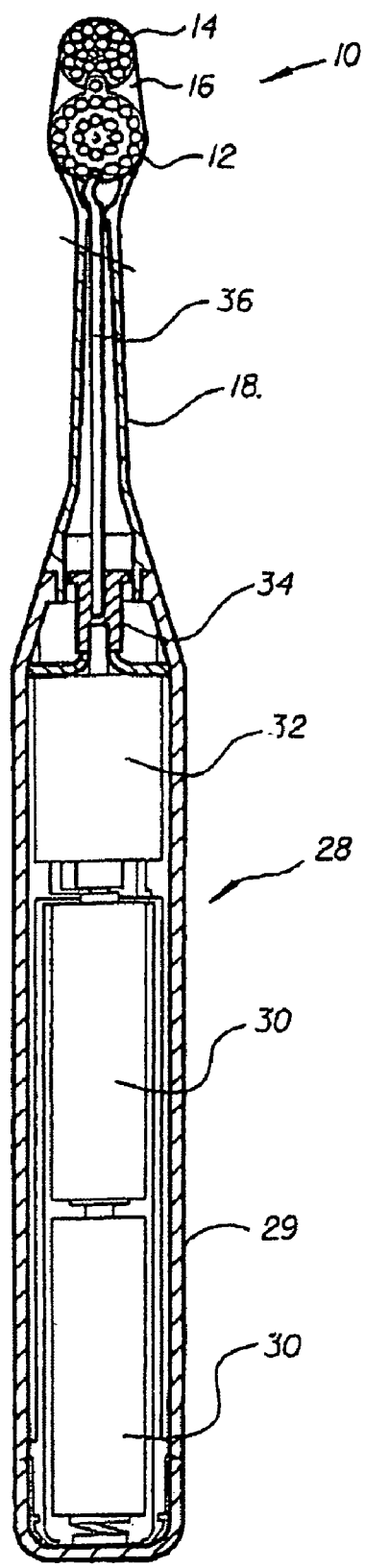
FIG. 8 is a cross-sectional plan view of a toothbrush incorporating the head shown in FIGS. 1-7.
Figure 9:
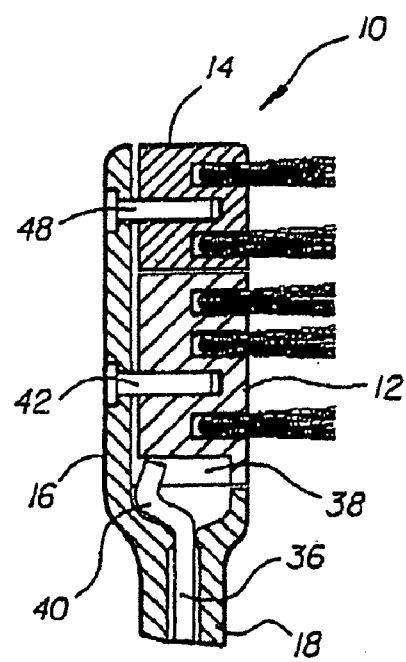
FIG. 9 is an enlarged side elevational view in cross-section of the head shown in FIGS. 1-8.

FIGS. 8-9 illustrate an exemplary type of drive structure for oscillating the primary tuft block 12. This drive structure incorporates the type of drive disclosed in U.S. Pat. No. 5,625,916, all of the details of which are incorporated herein by reference thereto. As shown in FIG. 8 the toothbrush 28 has a hollow housing 29 in which a plurality of batteries 30, 30 are mounted to power the motor 32 as actuated by an on/off switch (not shown). Motor 32 is connected to coupling 34 which grips one end of a drive shaft 36 so as to rotate the drive shaft 36.

As shown in FIG. 9 the primary tuft block 12 has a slot or opening 38 into which the offset crank end 40 of shaft 36 is mounted. As shaft 36 rotates the rotating crank end 40 causes the primary tuft block 12 to rotate in a back and forth oscillating manner about shaft or post 42 which is mounted to refill arm 16. Thus, the 360.degree. rotational movement of shaft 36 is transmitted into an oscillating back and forth rotational movement of primary tuft block 12.

The type of drive mechanism described and illustrated in FIGS. 8-9 is a particularly preferred type of drive mechanism because of its simplicity and its effectiveness. As shown, the drive shaft 36 extends axially from the motor 32 and is mounted directly to the primary tuft block 12. Accordingly, the primary tuft block 12 is oscillated by a drive which comprises an axially oriented shaft extending from the motor to the primary tuft block without the need for any intervening gears, etc. As used in this application the term "direct drive from a shaft axially extending from the motor to the primary tuft block" is intended to mean such a drive mechanism which does not require additional complicated structure such as gears and the like to oscillate the primary tuft block.

Figure 10A:
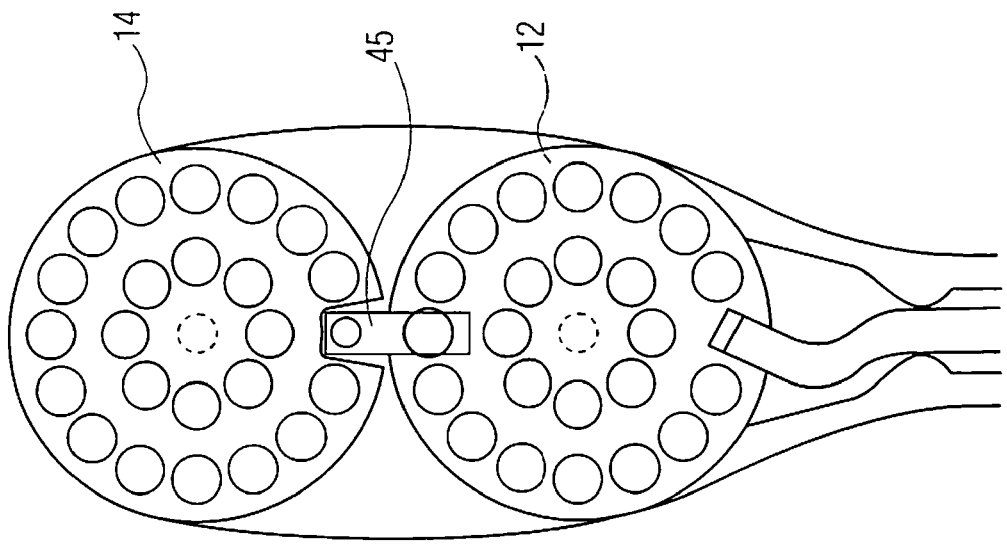
FIG. 10A is a view similar to FIG. 10 of a modified form of drive mechanism.
Figure 10:
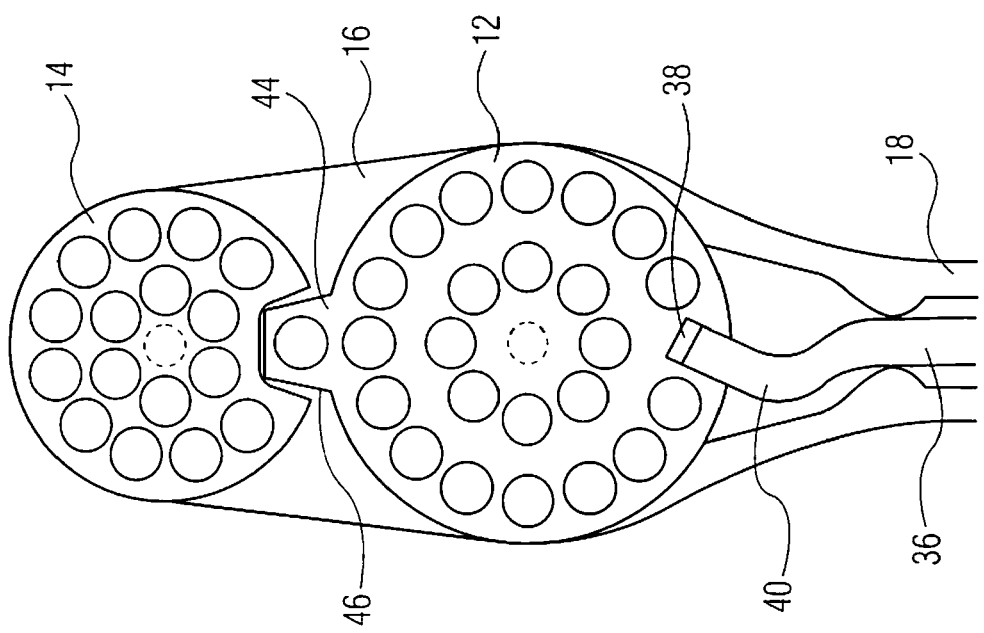
FIG. 10 is a top plan view showing the drive mechanism for the head shown in FIGS. 1-9.

FIG. 10 illustrates a drive connection between primary tuft block 12 and secondary tuft block 14. As shown therein primary tuft block 12 includes a finger or extension 44 which is located in slot or cutout 46 in secondary tuft block 14. Accordingly, as primary tuft block 12 reciprocates back and forth in a rotational manner the finger 44 causes a like oscillation to result from secondary tuft block 14. FIG. 9 illustrates the secondary tuft block 14 to be mounted on its post or shaft 48 secured to refill arm 16 to permit such oscillating rotational movement.

It is to be understood that while FIGS. 8-10 illustrate the oscillating movement of primary tuft block 12 to result from a rotating drive shaft 36 with its crank end 40, other types of oscillating drive mechanisms may be utilized as is known in the art such as gears, cams and the like. Such drive mechanisms, however, are less preferred.

Figure 10B:
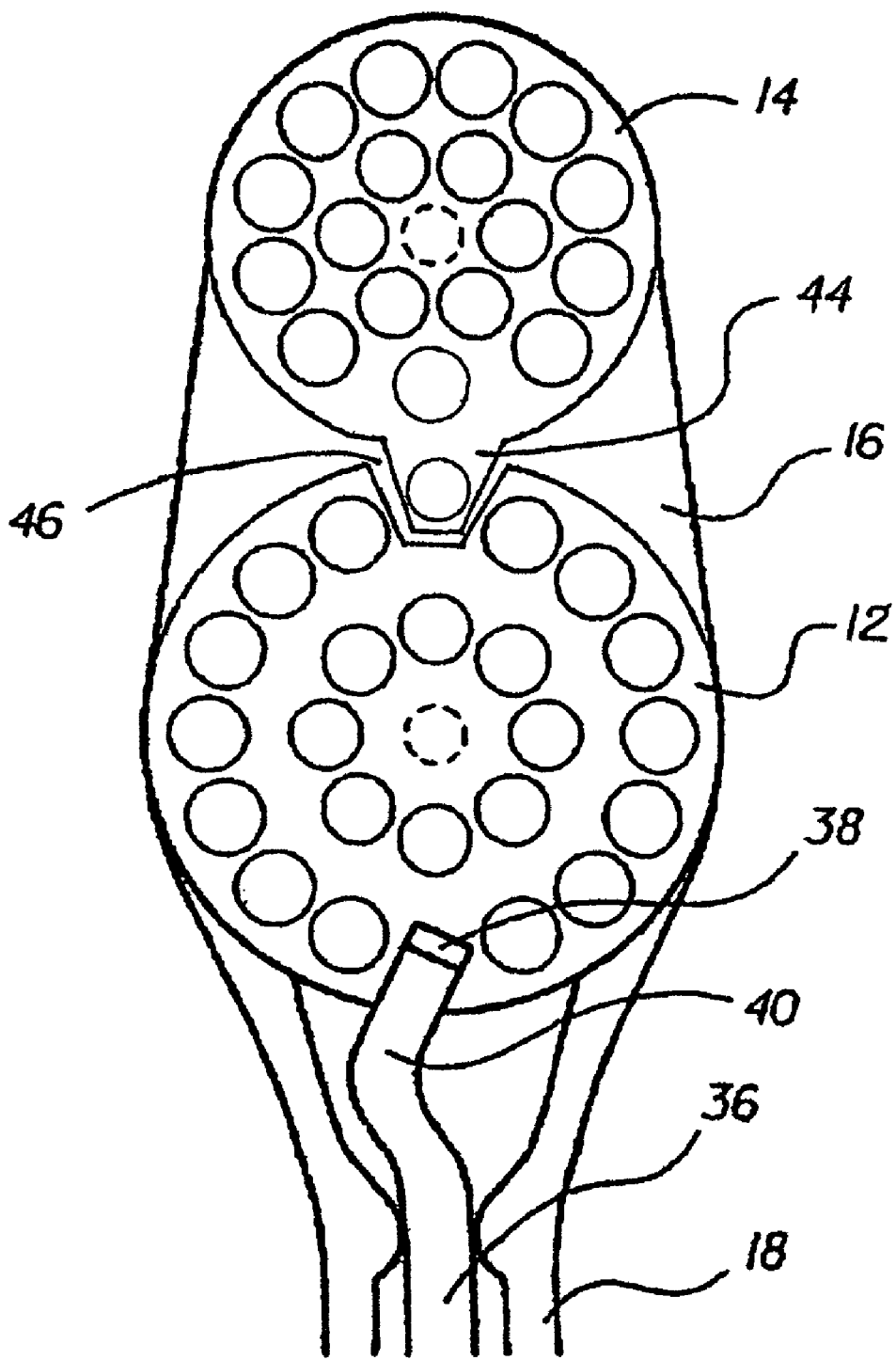
FIG. 10B is a top plan view showing an alternative drive mechanism for the head shown in FIGS. 1-9.
Figure 11:
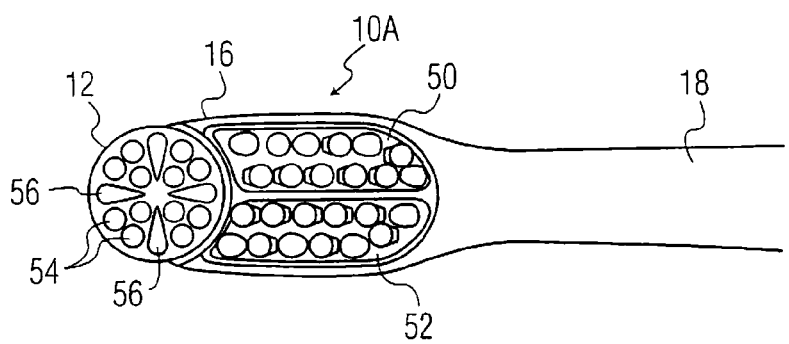
FIG. 11 is a top plan view of a powered toothbrush refill head in accordance with a further embodiment of this invention.

Similarly, while FIGS. 9-10 illustrate a preferred drive transmitting connection from the primary tuft block to the secondary tuft block by means of the finger 44 extending into cutout 46, the drive transmitting connection could be from a finger of the secondary tuft block located in a cutout in the primary tuft block (FIG. 10B). Alternatively, other types of drive transmitting transmissions or connections could also be used such as links or cams. FIG. 10A, for example, shows a pin 45 straddling the primary tuft block 12 and the secondary tuft block 14. Pin 45 could be pivotally secured to each tuft block 12, 14 so that an oscillating rotation of primary tuft block 12 would be transmitted to secondary tuft block 14 thereby causing an oscillating rotation in the opposite direction of secondary tuft block 14. Alternatively, pin 45 could be rigidly secured to or even integral with one of the tuft blocks and pivotally mounted to the other tuft block.

An advantageous aspect of the drive connection between primary tuft block 12 and secondary tuft block 14 is that primary tuft block 12 rotates back and forth only over a limited arc, rather than a full 360.degree. and that this oscillating or limited rotation is transmitted to the secondary tuft block to result in a like type of limited rotational oscillation. In the embodiment shown in FIG. 10 the oscillation of the secondary tuft block is achieved by a single drive connecting member, namely, the finger 44 mounted in the slot or cutout 46, rather than for example sets of intermeshed gear teeth. In the embodiment of FIG. 10A the drive connecting member is a pin 45.

The embodiment of FIGS. 1-10 thus utilizes a drive assembly in the handle of the toothbrush wherein the drive assembly includes a drive connection to the primary tuft block 12 so as to oscillate the primary tuft block 12 back and forth on its shaft 42. A drive transmitting connection, namely, the finger 44 and slot 46 or the pin 45 between the primary tuft block 12 and the secondary tuft block 14 results in moving the secondary tuft block 14 back and forth in an oscillating manner while the primary tuft block is oscillating.

It is to be understood that the invention in all of its embodiments could be practiced where the secondary tuft block also has a drive transmitting connection to still yet a further or tertiary tuft block. For example, the secondary and tertiary tuft blocks could utilize a similar type connection as the finger and slot that is utilized between the primary and secondary tuft blocks or by using any other suitable drive transmitting connection. The tertiary tuft block could drive yet a further tuft block, etc. The number of tuft blocks would be determined by space constraints and practicality. Having only a primary and a secondary tuft blocks is preferred.

Advantageously, the invention could be practiced with only minor constructional modification changes to existing type powered brush refill heads. Thus, for example, refill arm would be modified in shape to accept a second round tuft block 14 for connection with the primary round refill design or tuft block 12. This allows for simple modifications to the second head shape which could be a compact head, a regular head, full head, etc, so that different sizes/actions could be offered to the consumer.

The constructional changes that would be made to known powered refill products having a round oscillating block or primary tuft block would be to modify the shape of the refill arm 16 to accept the additional tuft plates which would be located below the round oscillating block 12. The round tuft block 12 would also require some modifications to accept the connection points for the additional plates. Other constructional modifications would depend on the different bristles configurations included in the consumer-preferred design (i.e. rubber fingers, etc.).

FIG. 10 illustrates the primary tuft block 12 to be of larger size than the secondary tuft block 14. FIG. 10A, however, shows a practice of the invention where both tuft blocks are of the same size. If desired, the secondary tuft block could be larger than the primary tuft block. It is particularly preferred to have both tuft blocks the same size since this lends itself to the possibility of making both tuft blocks of identical structure. This would simplify and reduce manufacturing costs. Thus, the slot 38 which accommodates the end 40 of shaft 36 for the primary tuft block could be used to function as the slot 46 of the secondary tuft block to accommodate the finger 44. Where both tuft blocks are made of identical structure the secondary tuft block would have a non-functioning finger. Where other types of drive transmitting members are used, such as pin 45, the secondary tuft block could still be provided with a non-functional slot identical to slot 38 of the primary tuft block so that the two tuft blocks are interchangeable during assembly.

FIGS. 11-20 relate to a further embodiment of this invention where there is at least one secondary tuft block at a location displaced from the primary tuft block. As shown in FIGS. 11-18 the head 10A includes a primary tuft block 12 and a secondary tuft block which is illustrated as being in the form of a pair of plates 50, 52 mounted on refill arm 16. As later described the two plates 50, 52 are mounted for reciprocating movement back and forth in a direction generally parallel to handle extension 18. This movement, in combination with the primary tuft block 12 oscillating rotationally, thereby allows the refill to deliver an added cleaning, polishing, whitening action in addition to the cleaning efficiency of a typical powered toothbrush refill product.

Figure 12:
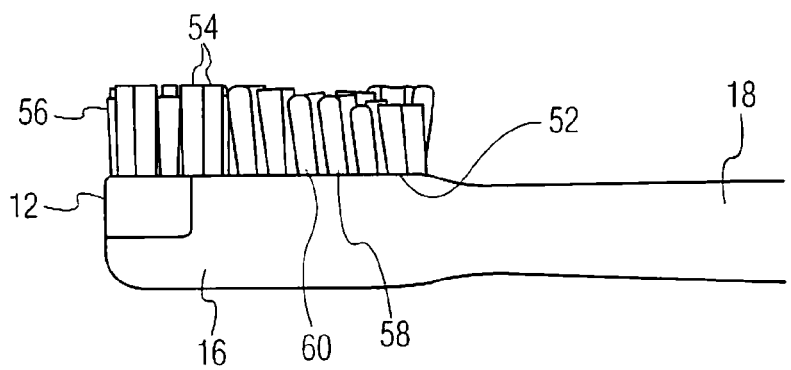
FIG. 12 is a side elevational view of the head shown in FIG. 11.
Figure 13:
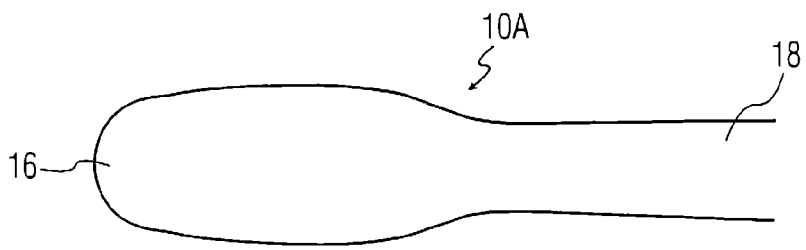
FIG. 13 is a bottom plan view of the head shown in FIGS. 11-12.
Figure 14:
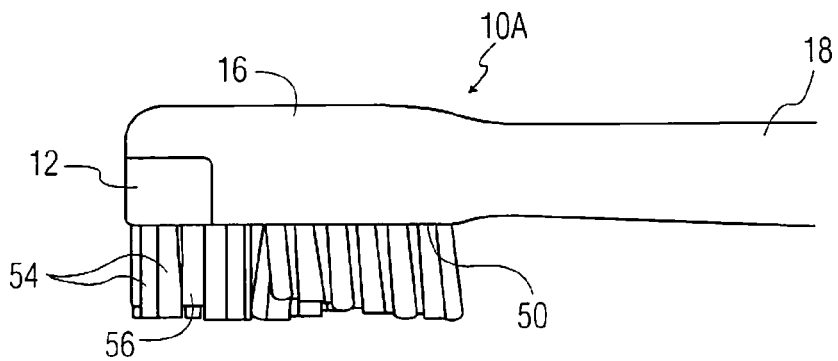
FIG. 14 is a side elevational view similar to FIG. 12 with the head inverted.
Figure 15:
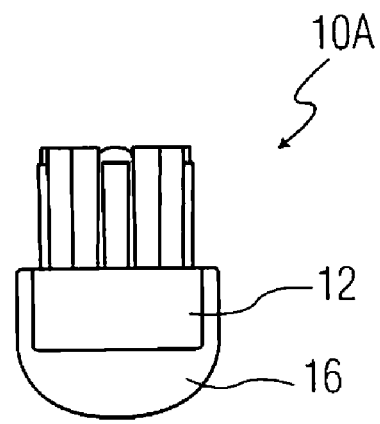
FIGS. 15-16 are end elevational views of the head shown in FIGS. 11-14.
Figure 16:
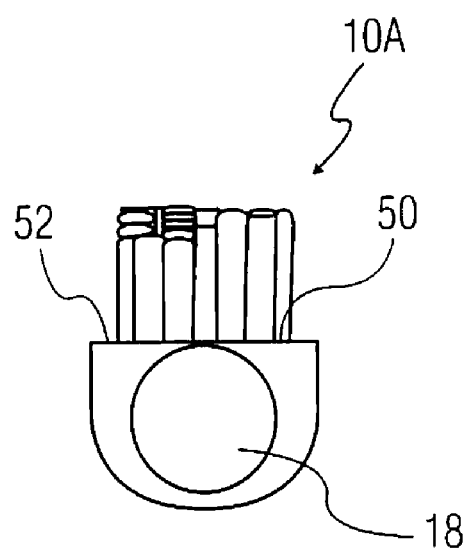
Figure 17:
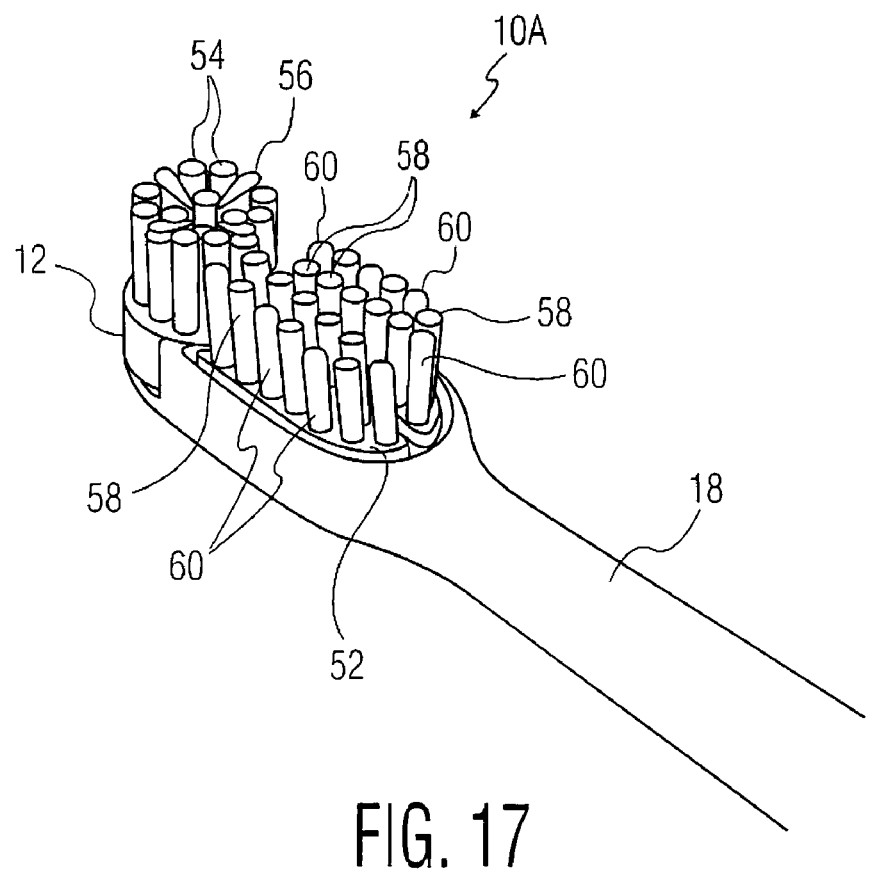
FIGS. 17-18 are perspective views showing the head of FIGS. 11-16 in the upright and inverted positions.
Figure 18:
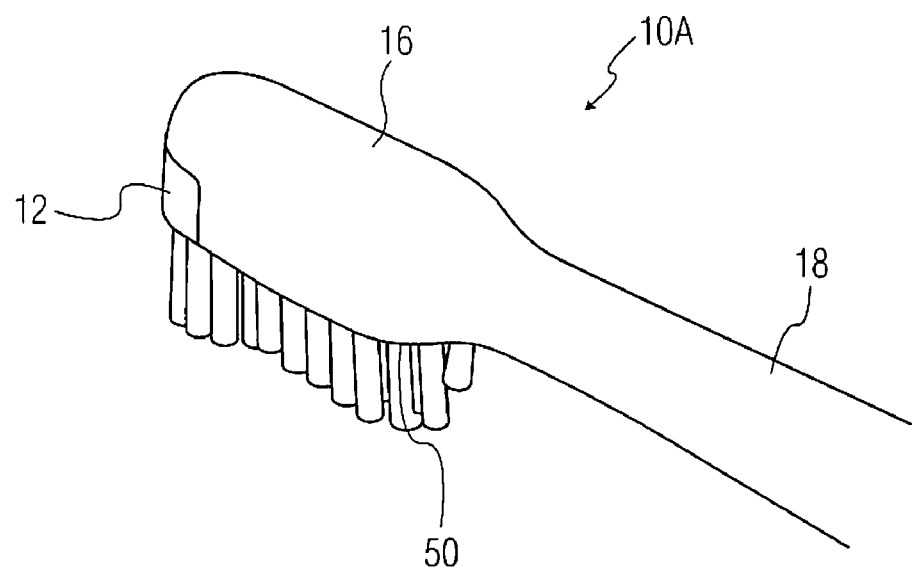

As with the description of the various bristle configurations and bristle material combination possibilities discussed with regard to head 10, the head 10A likewise could incorporate different combinations. In the illustrated embodiment, primary tuft block 12 includes a plurality of sets of natural bristles 54 separated by bristles of IMT block configuration 56. All of the bristles 54 are of the same height which is slightly higher than bristles 56. Plates 50, 52 include two longitudinal rows of bristles wherein the rows of bristles include natural bristles 58 and rubber fingers/bristles 60. The height of the bristles for each plate 50, 52 tapers so as to create a ramp effect. Thus, the bristles for plate 50 are higher at the end of plate 50 located nearer to handle extension 18 creating a downwardly inclined ramp toward primary tuft block 12. The bristles in plate 52, however, have the opposite ramp effect where the tallest bristles are closest to primary tuft block 12. In addition to the bristles in plates 50, 52 tapering in height, the bristles may also be inclined toward and away from the handle as best shown in FIG. 12.

Figure 19:
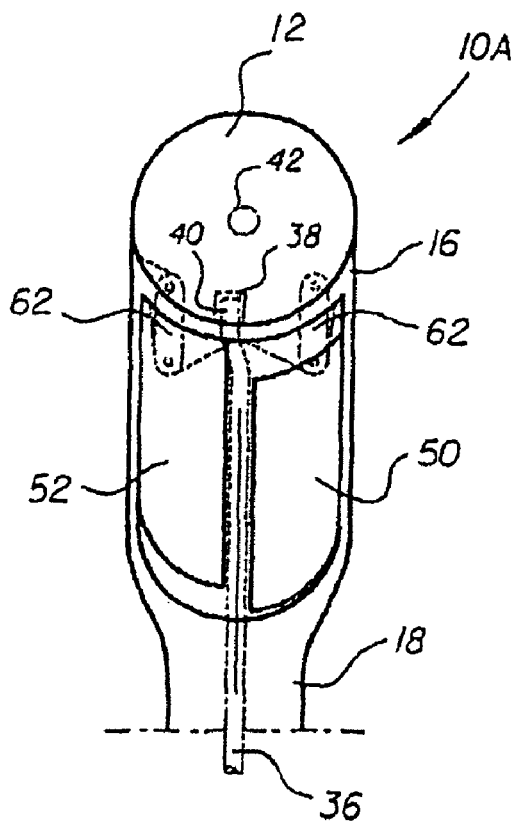
FIGS. 19-20 are plan views of the drive mechanism for the head shown in FIGS. 11-18 in different phases of operation.
Figure 20:
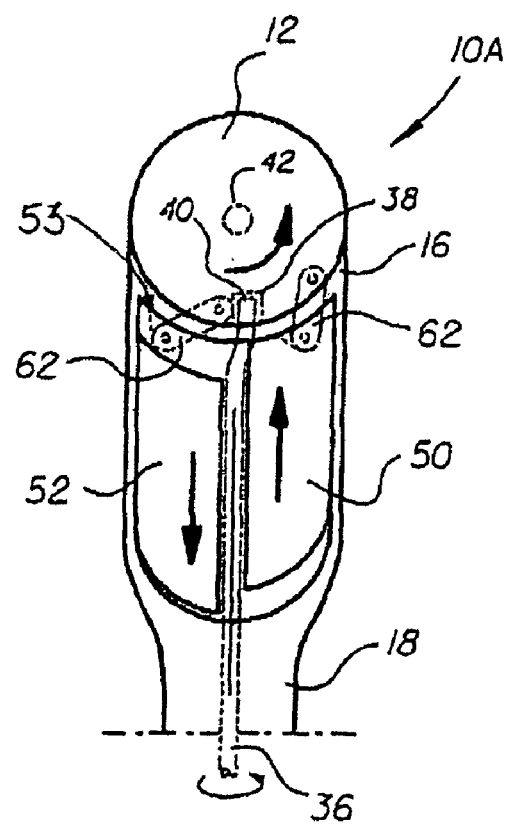
Figure 26:
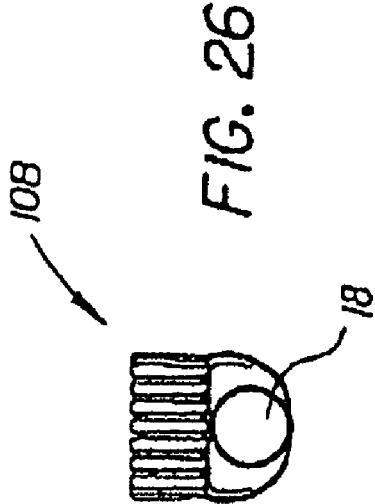
FIGS. 25-26 are end elevational views of the head shown in FIGS. 21-24.
Figure 25:
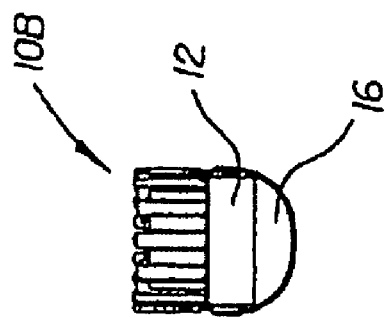
Figure 27:
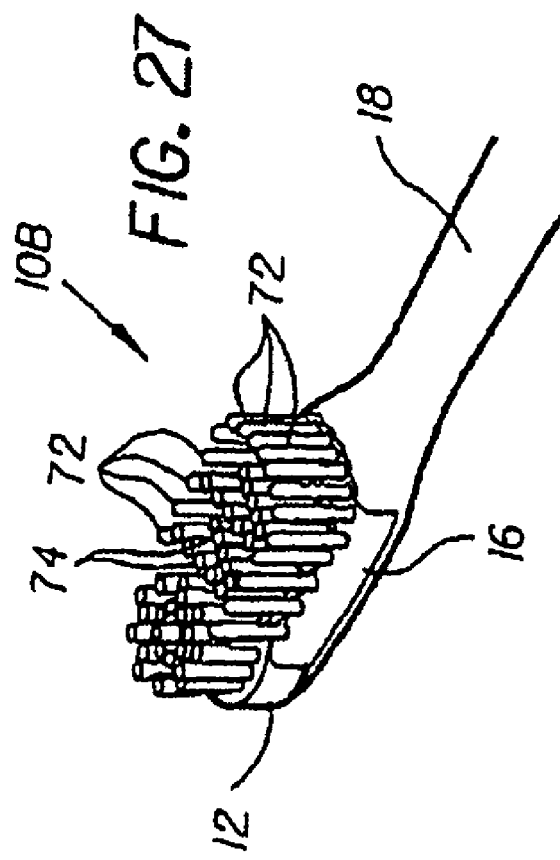
FIGS. 27-28 are perspective views of the head shown in FIGS. 21-26 in the upright and inverted positions.
Figure 28:
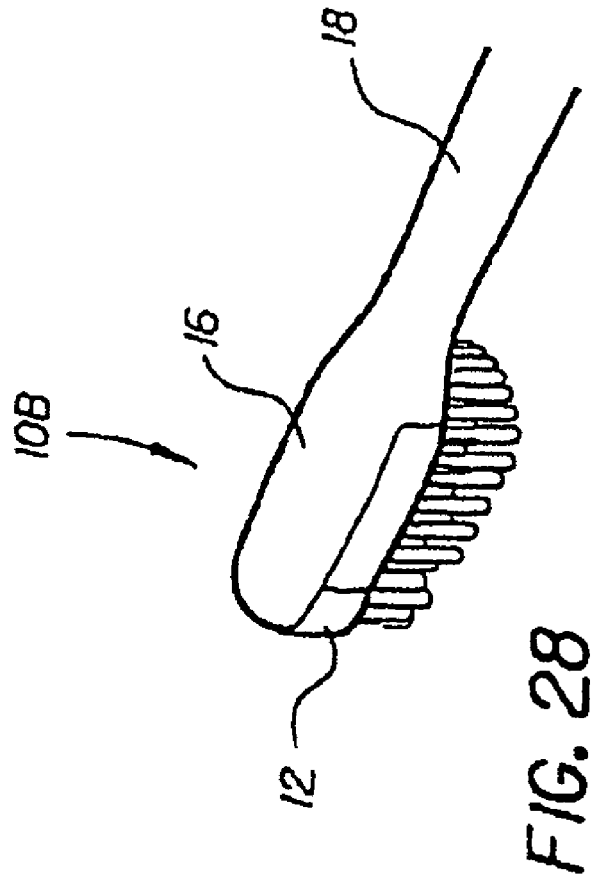
Figure 33:
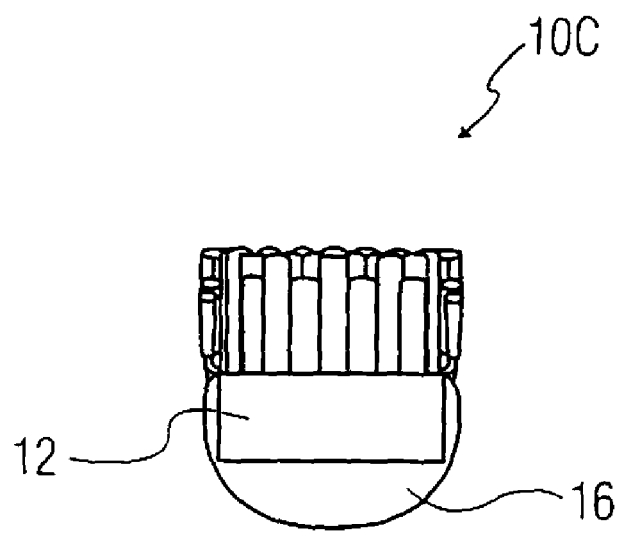
FIGS. 33-34 are end elevational views of the head shown in FIGS. 29-32.
Figure 34:
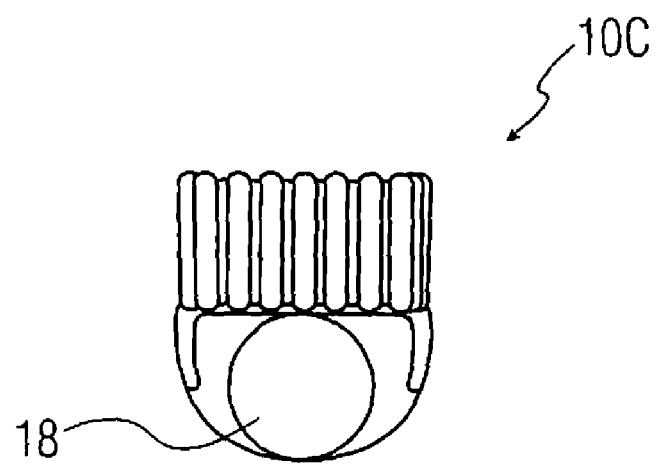
Figure 35:
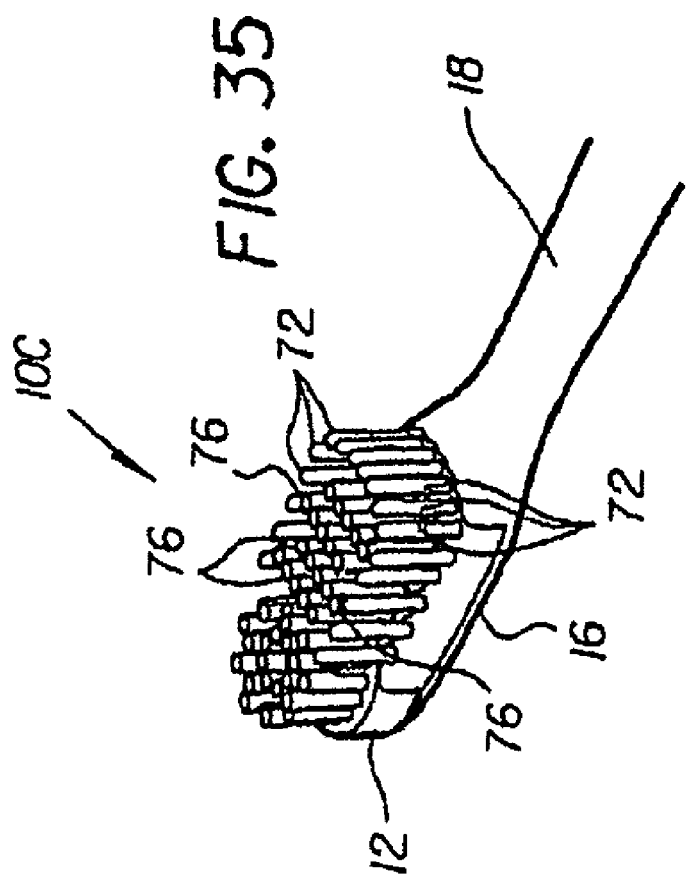
FIGS. 35-36 are perspective views of the head shown in FIGS. 29-34 in the upright and inverted positions.
Figure 36:
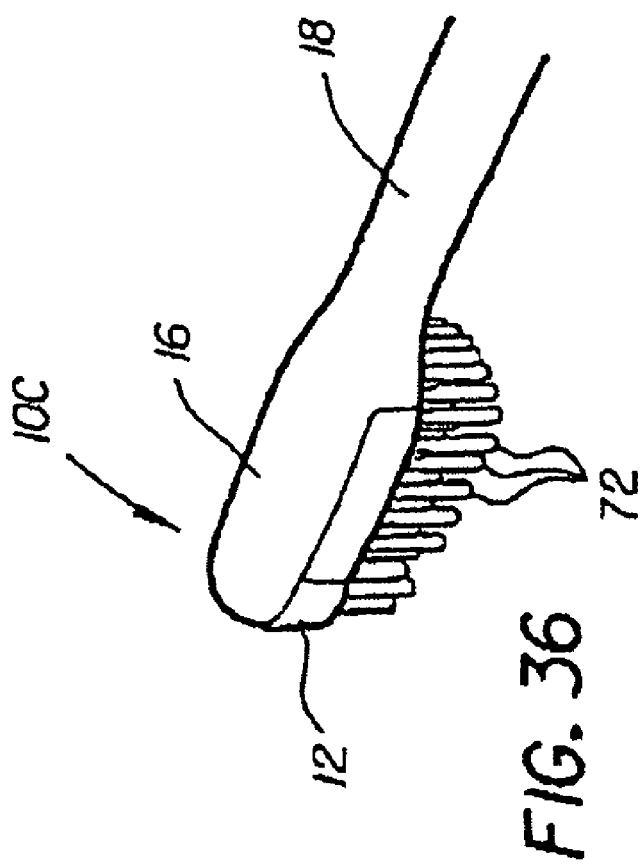
Figure 42:
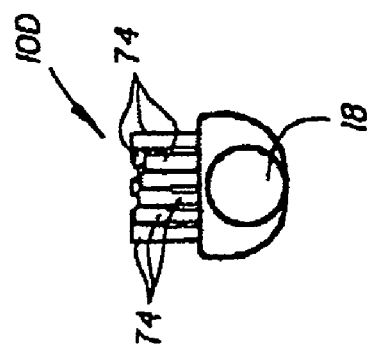
FIGS. 41-42 are end elevational views of the head shown in FIGS. 37-40.
Figure 41:
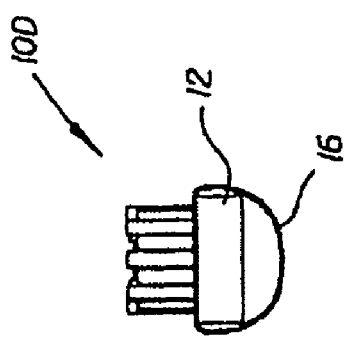
Figure 43:
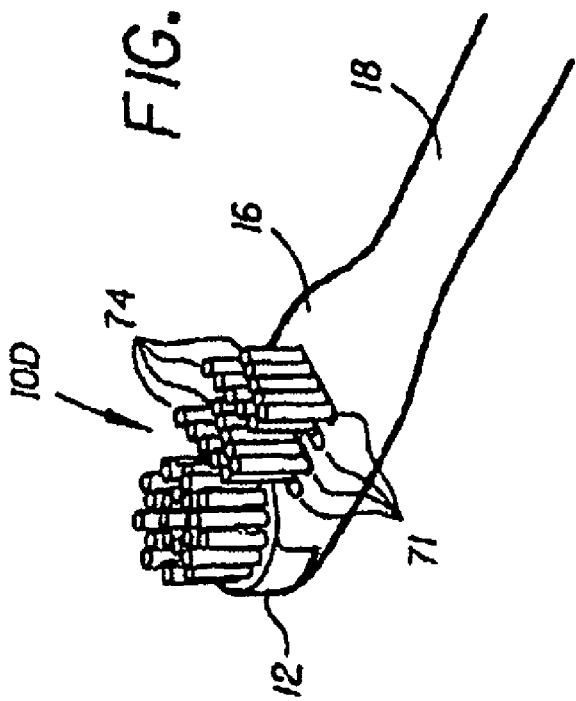
FIGS. 43-44 are perspective views of the head shown in FIGS. 37-42 in the upright and inverted positions.
Figure 44:
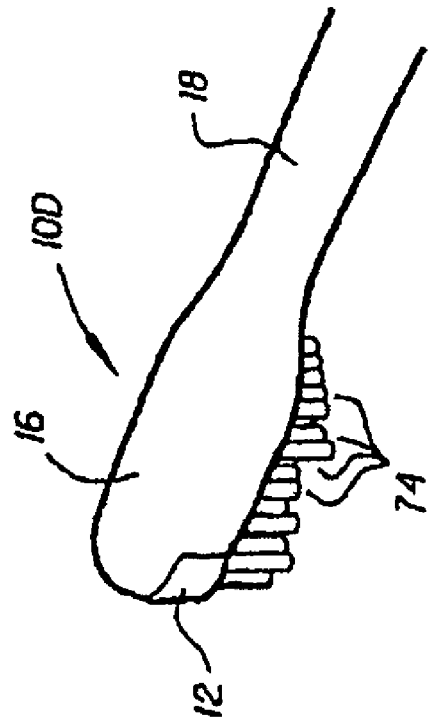
Figure 50:
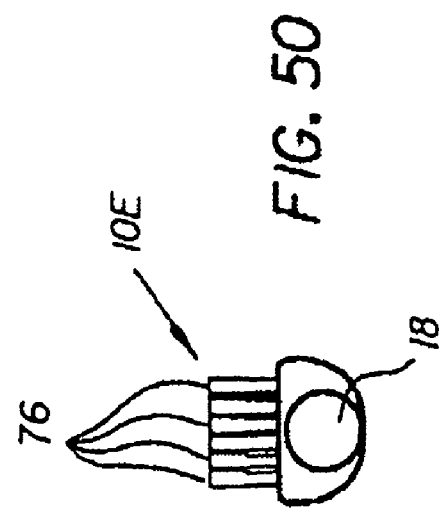
FIGS. 49-50 are end elevational views of the head shown in FIGS. 45-48.
Figure 49:
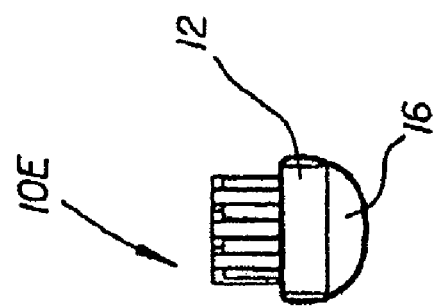
Figure 51:
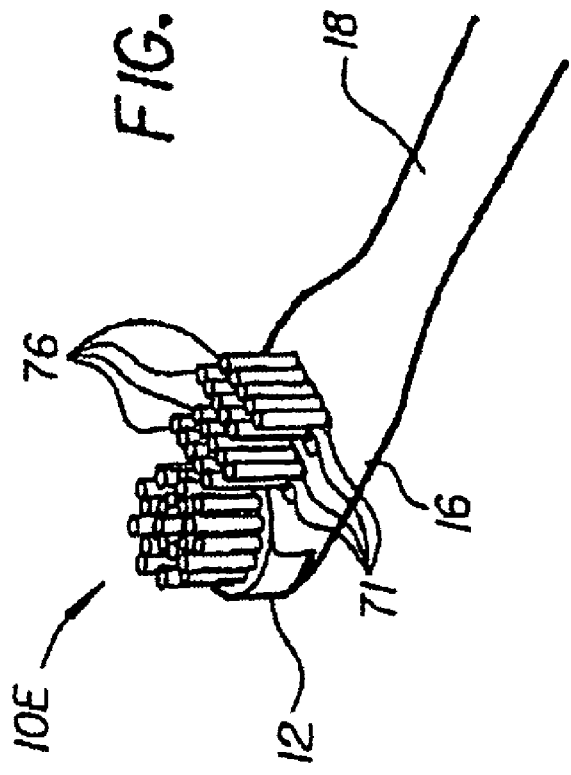
FIGS. 51-52 are perspective views of the head shown in FIGS. 45-50 in the upright and inverted positions.
Figure 52:
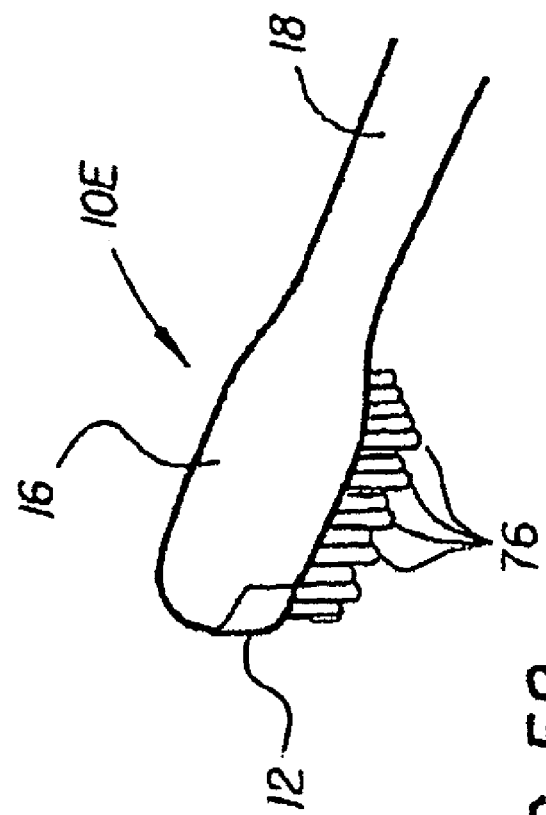

FIGS. 19-20 illustrate a drive mechanism for causing the plates 50, 52 to reciprocate linearly in the same direction as handle extension 18 while the primary tuft block 12 oscillates back and forth rotationally. As shown in FIGS. 19-20 the drive connection is located below the outer surface of the primary tuft block 12 and the outer surface of the secondary tuft block from which the bristles extend outwardly away from refill arm 16. As with the embodiment of FIGS. 8-10 the handle 18 includes a rotating drive shaft 36 which has a crank end 40 engaged in slot 38 of primary tuft block 12 so that rotation of drive shaft 36 causes the primary tuft block 12 to rotate about its shaft or post 42. Thus, the drive mechanism is preferably a direct drive from a shaft extending from the motor to the primary tuft block.

The plates 50, 52 are connected to oscillating primary tuft block 12 in such a manner that the rotational movement of primary tuft block 12 causes the plates to reciprocate back and forth in a direction parallel to handle extension 18. As illustrated in FIGS. 19-20 the connection is accomplished by a link 62 connecting each plate 50, 52 to primary tuft block 12. FIG. 19 shows the plates in a neutral or centered condition. FIG. 20 shows the condition where the primary tuft block 12 is rotating in a counterclockwise direction. The crank end 40 is shifted to the right as shown in FIG. 20. The links 62, 62 cause the plate 50 to be pulled in a direction away from handle extension 18, while the plate 52 is pushed in a direction toward the handle extension. Alternatively, the links could be mounted in such a manner that both plates 50, 52 move simultaneously in the same direction. If desired, plates 50, 52 could be mounted in tracks in refill arm 16 to assure that the movement of the plates is a straight back and forth linear movement thereby avoiding any side shifting or rotation.

In order to minimize space requirements the outer edge 53 of each plate 50, 52 which is disposed adjacent to the primary tuft block 12 is arcuate along an arc generally parallel to the curvature of the round or circular primary tuft block 12.

Although FIGS. 11-20 illustrate the secondary tuft block to be in the form of two side by side plates the invention may be practiced with other variations wherein there is an up and down movement parallel to the longitudinal axis of the handle extension 18. Thus, in its simplest form there could be a single plate or there could be three or more side by side plates where some or all of the plates move in the same or in different directions. For example, two or more adjacent plates could move in the same direction. Alternatively, each plate may move in an opposite direction to its adjacent plate. In each of these variations the necessary points of connection would be made between each plate and the oscillating primary tuft block to cause the linear reciprocating movement of the plates and their outwardly extending bristles.

As is illustratively shown in FIGS. 11-20 in at least one embodiment of the invention, the aforedescribed secondary tuft block includes two tuft plates 50, 52 configured to sit and be used in substantially the same plane. As is illustrated for example in FIGS. 19-20, the tuft plates 50, 52 are shown as being moved linearly in opposing directions as illustrated by the motion arrows in substantially the same plane. Accordingly, tuft plates 50, 52 may be characterized as being substantially coplanar as they rest and move in a single plane. This coplanar configuration, position, and movement facilitates cleaning characteristics and capabilities associated with the brush and further assists the secondary tuft block to have a generally contiguous and planar surface allowing for outwardly extending bristles to have various patterns including a uniform pattern of varying types and to also provide a generally uniform surface to prevent debris, toothpaste and other particles from collecting in uneven surfaces that would otherwise occur. Additionally, this configuration permits movement assisting to improve cleaning while preventing particles, which could disrupt or halt movement mechanisms, from reaching interior components.

FIGS. 21-56 illustrate a third variation of the invention wherein there is a reciprocating movement of a secondary tuft block at a location displaced from the primary tuft block while the primary tuft block rotates in an oscillating manner. In the various embodiments of FIGS. 21-56 the oscillating or reciprocating movement is a side to side movement in a direction perpendicular to the longitudinal axis of the handle extension 18. FIGS. 21-52 illustrate various exemplary possible combinations of bristle structure that could be used with this practice of the invention. One such combination of bristle structure is illustrated in FIGS. 21-28. As shown therein the head includes a primary tuft block 12 with the secondary tuft block being formed by parallel laterally disposed bars 64,66, 68,70. (The bars 64,66,68,70 are actually located below the surface with the bristles on the bars extending outwardly through slots in refill arm 16.)

FIGS. 21-28 illustrate head 10B with one variation of bristle combination. As shown therein, a set of stimulators 72 is arranged around the periphery of refill arm 16 outwardly of the laterally reciprocating bristle bars 64,66,68,70. The bristles 74 on the bristle bars taper in height to create a ramped affect. The tapering may be uniform in the sense that the bristles in each row taper in the same direction laterally across head 10B or the tapering may alternate from row to row or the tapering could be such that the bristles 74 in rows or on bars 68 and 70 are the same as each other while being opposite to the tapering for the bristles on bars 64, 66. (FIG. 43 also illustrates the ramped bristles 74 without peripheral stimulators 72.)

In the embodiment shown in FIGS. 29-36 the head 10C also includes a set of peripherally located stimulators 72. The bristles 76 for laterally oscillating bars 64, 66, 68 and 70, however, are all of the same height, rather than being ramped.

FIGS. 37-44 illustrate a variation where the head 10D has its bristles 74 of tapering height to create a ramp effect for each laterally oscillating bar 64,66,68,70 in the same manner as described with regard to head 10B. Unlike head 10B, however, head 10D omits the peripherally located stimulators.

FIGS. 45-52 illustrate a head 10E which is similar to head 10C in that the bristles 76 are of the same height but the head does not include any stimulators surrounding the bristles 76.

As illustrated, particularly in FIGS. 21, 29, 37, 43, 45 and 51, the bristles 74 or 76 extend outwardly from the refill arm 16 through slots 71 formed in the refill arm with the rows of bristles being mounted on the bars which are actually located below the outer surface of refill arm 16.

Figure 53:
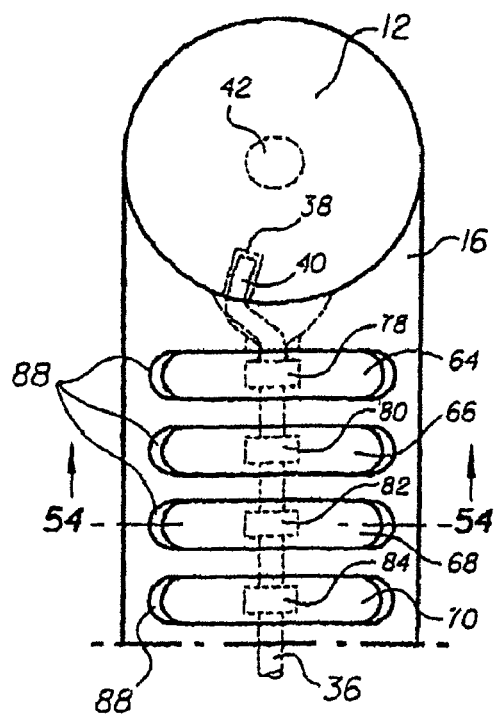
FIG. 53 is a plan view of the drive mechanism for the heads shown in FIGS. 21-52 in one phase of operation.
Figure 55:
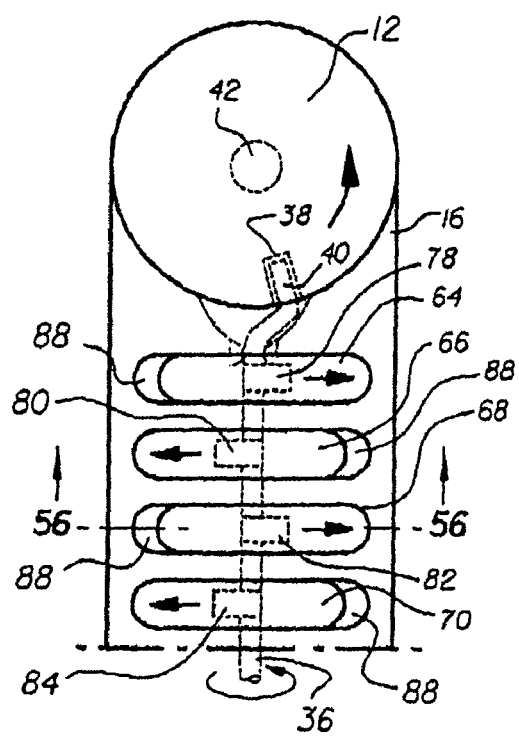
FIG. 55 is a view similar to FIG. 53 showing a different phase of operation.
Figure 54:
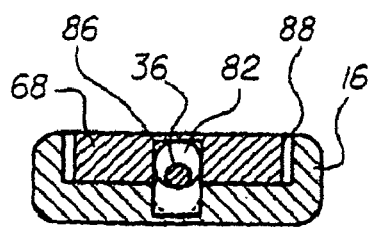
FIG. 54 is a cross-sectional view taken through FIG. 53 along the line 54-54.
Figure 56:
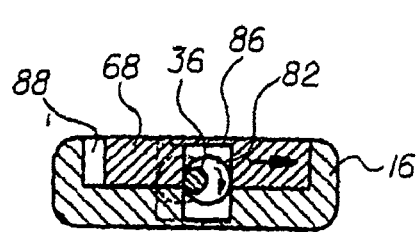
FIG. 56 is a cross-sectional view taken through FIG. 55 along the line 56-56.

FIGS. 53-56 illustrate one technique for causing the laterally arranged bars 64, 66, 68 and 70 to reciprocate back and forth while the primary tuft block 12 reciprocates rotationally. As shown therein, and as previously described, the drive shaft 36 has its crank end 40 mounted in slot 38 of primary tuft block 12 to cause the primary tuft block 12 to oscillate rotationally on its post or shaft 42. This drive assembly which includes the rotating shaft 36 and its drive connection 38, 40 thus causes the primary tuft block 12 to oscillate back and forth. A drive transmitting connection between the primary tuft block 12 and the secondary tuft block formed by bars 64,66,68 and 70 is achieved through the use of cams 78,80, 82,84 mounted on drive shaft 36. FIGS. 54 and 56 illustrate how the cam 82 associated with bar 68 causes the bar to shift laterally while drive shaft 36 rotates. As shown therein, the refill arm 16 includes a recess 88 of sufficient size to permit the lateral back and forth shifting in a direction perpendicular to drive shaft 36 and the longitudinal axis of handle extension 18. Cam 82 is located in a slot or cutout 86 in bar 68. As shown in FIG. 54 the cam 82 is in its centered condition with the cam located upwardly from drive shaft 36. FIG. 54 also shows in phantom the cam rotated 180.degree. which would still result in the bar 68 being in its centered condition.

FIG. 56 illustrates in solid lines the cam 82 rotated 90.degree. from its centered condition which in FIG. 56 would cause the bar 68 to shift to the right to its extreme right-hand most position. FIG. 56 shows in phantom the position of the cam and the slot or cutout 86 when the cam 82 is shifted 180.degree. from the position shown in FIG. 56 which would then cause the bar 68 to be shifted to its extreme leftmost position. Accordingly, while shaft 36 rotates 360.degree. this rotation is transmitted by crank end 40 to cause a rotational oscillation of primary tuft block 12 and the rotating cam 82 causes a lateral oscillation of bar 68.

Cam 82 and cam 78 are mounted identically to each other on shaft 36. As a result bars 64 and 68 move in unison in the same direction as each other. Conversely, cams 80 and 84 are configured and mounted to be opposite cams 78 and 82 as shown in FIG. 55 so that when bars 64 and 68 move toward the right under the influence of their cams 78 and 82 the bars 66 and 70 move toward the left under their influence of their cams 80 and 84.

Figure 55A:
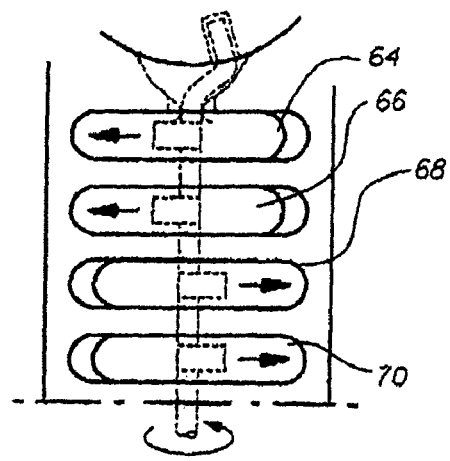
FIG. 55A is a view similar to FIG. 55 of a modified mode of operation.

FIG. 55 illustrates each bar to be moved in a direction opposite to its adjacent bar. FIG. 55A, however, shows a variation wherein the cams are arranged so that pairs of adjacent bars move in the same direction. Thus, as shown in FIG. 55A the bars 64 and 66 move in the same direction while adjacent bars 68, 70 move in the opposite direction.

If desired, the invention could be practiced with only a single bar moving back and forth in a lateral direction perpendicular to the longitudinal axis of handle 18. Preferably, however, sets of pairs of bars (such as illustrated in FIGS. 53, 55 and 55A) are the preferred practice of this invention. Each set of bars could be alternately arranged bars (as in FIG. 55) or could be adjacent bars (as in FIG. 55A). The invention, however, could be practiced with greater or lesser number of bars arranged in pairs or arranged for individual movement by modifying the cam location and shape on shaft 36. For example, a total of six reciprocating bars could be used arranged in two sets each having three alternately located bars or in three sets of adjacent bars. Such arrangement, however, would require a larger head size. The cams could also be located on shaft 36 so that, for example, each of the cams 78, 80, 82 and 84 is located on shaft 36 in a different angular orientation from each other whereby each of the bars would be oscillated out of unison with the other bars.

The various embodiments of FIGS. 21-56 may thus be practiced by modifying the drive shaft 36 to create a cam action to drive a series of horizontally aligned bristle rows. Preferably, the bristle rows 64,66,68,70 are connected into two subsets 64, 68 and 66, 70 that operate in opposing directions as the drive shaft 36 rotates. This resulting action in combination with the round oscillating block 12 creates enough movement to deliver additional oral health benefits like more efficacious cleaning, tooth polishing, and/or tooth whitening. The additional movements can also be enhanced by different bristle configurations and bristle materials as described. Further, by surrounding the bristles with rubber fingers 72 the fingers provide gum massage in addition to the action supplied by the extra bristle rows.

The construction changes that would be necessary to accomplish this new action would include a modification to the shape of the refill arm to accept the additional tuft blocks or bars located below the round oscillating block. The drive shaft would also be modified to create the cam action to drive the additional blocks. Other construction modifications would depend on the different bristle configurations included in the consumer-preferred design.

Where ramped bristles 74 are used, in addition to tapering the height of the bristles, the bristles could also be inclined either in the same or opposite to the inclination of the adjacent rows of bristles. Alternatively, the rows of bristles could include ramped bristles for one row with bristles of equal height for an adjacent row. Still further, instead of using individual tufts of bristles for a row a single cleaning element, such as an elongated rubber finger, could be used for one or more of the rows.

The invention has been described with respect to three different embodiments wherein in addition to the oscillation of the primary tuft block there is also an oscillation either rotationally or linearly in the same direction as the longitudinal axis of the handle or linearly in a direction perpendicular to the longitudinal axis of the handle. The invention, however, may also be practiced where combinations of those forms of oscillation are achieved. Thus, for example, the side to side type of oscillation illustrated in FIGS. 53-56 could be accomplished by the utilization of cams on the drive shaft while the primary tuft block also causes either rotational and/or longitudinal linear oscillation as in the other embodiments or any combination thereof. The invention may also be practiced where instead of rotating, the primary tuft block oscillates back and forth parallel to the handle or side to side, although a rotational oscillation is preferred. It is also to be understood that while the invention has been described in its preferred manner of causing oscillation of the secondary tuft blocks other types of drive mechanisms may be used within the spirit of this invention.

What is claimed:

1. A powered toothbrush comprising:
   a handle;
   a head mounted to said handle;
   a primary tuft block mounted in said head, said primary tuft block having bristles extending outwardly from an exposed face of said head;
   a shaft mounted in said head, said primary tuft block being rotationally mounted on said shaft;
   a secondary tuft block mounted in said head at a location displaced from said primary tuft block;
   wherein said primary tuft block has a generally circular cross-section, and said secondary tuft block having a plurality of horizontally disposed bars located generally perpendicular to said handle, each of said bars having bristles extending outwardly therefrom, each of said bars being disposed within a horizontally elongated slot formed in said exposed face of said head and having a length that is less than a length of said horizontally elongated slot, such that each of said bars is movable within said horizontally elongated slot from one side of said horizontally elongated slot to an opposing side of said horizontally elongated slot;
   a drive shaft connected to said primary tuft block to oscillate said primary tuft block back and forth in a rotational manner; and
   said drive shaft creating a cam action that moves said bars horizontally within said horizontally elongated slots in a reciprocating manner in a linear direction perpendicular to said handle while said primary tuft block is oscillated and wherein adjacent bars move in opposite directions.

2. The toothbrush of claim 1 wherein said bars are coplanar.

3. The toothbrush of claim 2 wherein said plurality of bars comprises at least two sets of bars, each of said sets of bars having at least two bars in said set, and said bars of said at least two sets being mounted in an alternating manner with a bar of each set disposed adjacent to a bar of the other set.

4. The toothbrush of claim 2 wherein said plurality of bars comprises two sets of side by side bars, each of said sets having two bars, and said sets of bars being mounted in an alternating manner whereby a bar of each of said sets is disposed adjacent to a bar of the other of said sets.

5. The toothbrush of claim 2 wherein said plurality of bars comprises at least two sets of bars, each of said sets of bars having at least two adjacent bars in said set, and each of said sets of adjacent bars being mounted to move in a direction opposite to the movement of its adjacent set of bars.

6. The toothbrush of claim 2 wherein said plurality of bars comprises two sets of side by side parallel bars, each of said sets having two adjacent bars, and each of said sets of adjacent bars being mounted to move in a direction opposite to the direction of movement of the other of said sets of adjacent bars.

7. The toothbrush of claim 2 wherein said drive shaft comprises a crank end mounted to said primary tuft block.

8. The toothbrush of claim 2 wherein said bristles on said bars are of ramped height arranged in rows parallel to each other.

9. The toothbrush of claim 8 wherein a direction of inclination of each row of bristles is opposite to its adjacent row.

10. The toothbrush of claim 8 including stimulator bristles on said head positioned peripherally outwardly of and at least partially around said secondary tuft block.

11. The toothbrush of claim 2 wherein said bristles on said bars are all of the same height.

12. The toothbrush of claim 11 including stimulator bristles on said head positioned peripherally outwardly of and at least partially around said secondary tuft block.

13. The toothbrush of claim 2 wherein said bars are located between said primary tuft block and said handle, and further wherein said bristles on at least one of said primary tuft block and said secondary tuft block include bristles of different configuration and material than other bristles on said at least one of said primary tuft block and said secondary tuft block.

14. The toothbrush of claim 1 wherein said cam action moves the exposed bristles of said bars in the linear direction perpendicular to said handle, and wherein the exposed bristles of said bars maintain an orientation that is substantially perpendicular to said exposed face of said head during said cam action.

* * * * *